US008583450B2

(12) United States Patent
Baker et al.

(10) Patent No.: US 8,583,450 B2
(45) Date of Patent: Nov. 12, 2013

(54) DOCTOR PERFORMANCE EVALUATION TOOL FOR CONSUMERS

(75) Inventors: Geoffrey Baker, San Francisco, CA (US); Pamela Rollins, Dallas, TX (US)

(73) Assignee: IMS Health Incorporated, Danbury, CT (US)

( * ) Notice: Subject to any disclaimer, the term of this patent is extended or adjusted under 35 U.S.C. 154(b) by 1507 days.

(21) Appl. No.: 11/316,335

(22) Filed: Dec. 22, 2005

(65) Prior Publication Data

US 2006/0161456 A1 Jul. 20, 2006

Related U.S. Application Data

(63) Continuation-in-part of application No. 11/192,999, filed on Jul. 29, 2005, now abandoned.

(60) Provisional application No. 60/592,283, filed on Jul. 29, 2004.

(51) Int. Cl.
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| | | | |
|---|---|---|---|
| 5,557,514 A | 9/1996 | Seare et al. | |
| 5,652,842 A | 7/1997 | Siegrist, Jr. et al. | |
| 5,706,441 A | 1/1998 | Lockwood | |
| 6,223,164 B1 | 4/2001 | Seare et al. | |
| 6,338,042 B1 * | 1/2002 | Paizis | 705/7.37 |
| 7,739,126 B1 * | 6/2010 | Cave et al. | 705/2 |
| 2003/0163349 A1 * | 8/2003 | Ho | 705/2 |

FOREIGN PATENT DOCUMENTS

WO WO 03/032192 A1 * 4/2003

* cited by examiner

*Primary Examiner* — Gerald J. O'Connor
*Assistant Examiner* — Neha Patel
(74) *Attorney, Agent, or Firm* — Fish & Richardson P.C.

(57) ABSTRACT

Presenting information to patients—intuitive, statistically significant bucket rankings in more than one score domain—in response to requests for medical providers associated with their choice of medical conditions or treatments, and other restrictions. Statistically significant intuitive bucket rankings (such as "*" to "****") from relatively limited data on medical providers, and adjusting those intuitive bucket rankings so that they reflect a valid measure of the domain of interest despite differing numbers of measurements available for distinct medical providers. User interface by which a patient can (1) specify medical conditions or treatments, and other restrictions, (2) search for medical providers appropriate to those conditions, order them by bucket ranking in a choice of score domain, and (3) obtain more information on those medical conditions or treatments, for medical providers the patient selects.

15 Claims, 23 Drawing Sheets

| Product Name and current screen location is displayed here | | | | | | | |
|---|---|---|---|---|---|---|---|
| Toolbar/Menu Bar | | | | | | | |
| Software product owner's name. E.g. Humana | Displays user's current screen/menu location | | | | | | |
| | Select Physician by Rating | Physician Selection by your Condition | Select Physician by Your Surgery or Procedure | Estimate Your Medical Costs | Prepare for your Physician Visit | Evaluate Your Care | Hospital Search By Condition | Health Categories |
| | User navigation and current screen location | | | | | | |

Search by Rating

This area displays user-selectable search criteria selection in the form of drop-down boxes, radio buttons, and the like for searching for a physician by rating.

View Ratings

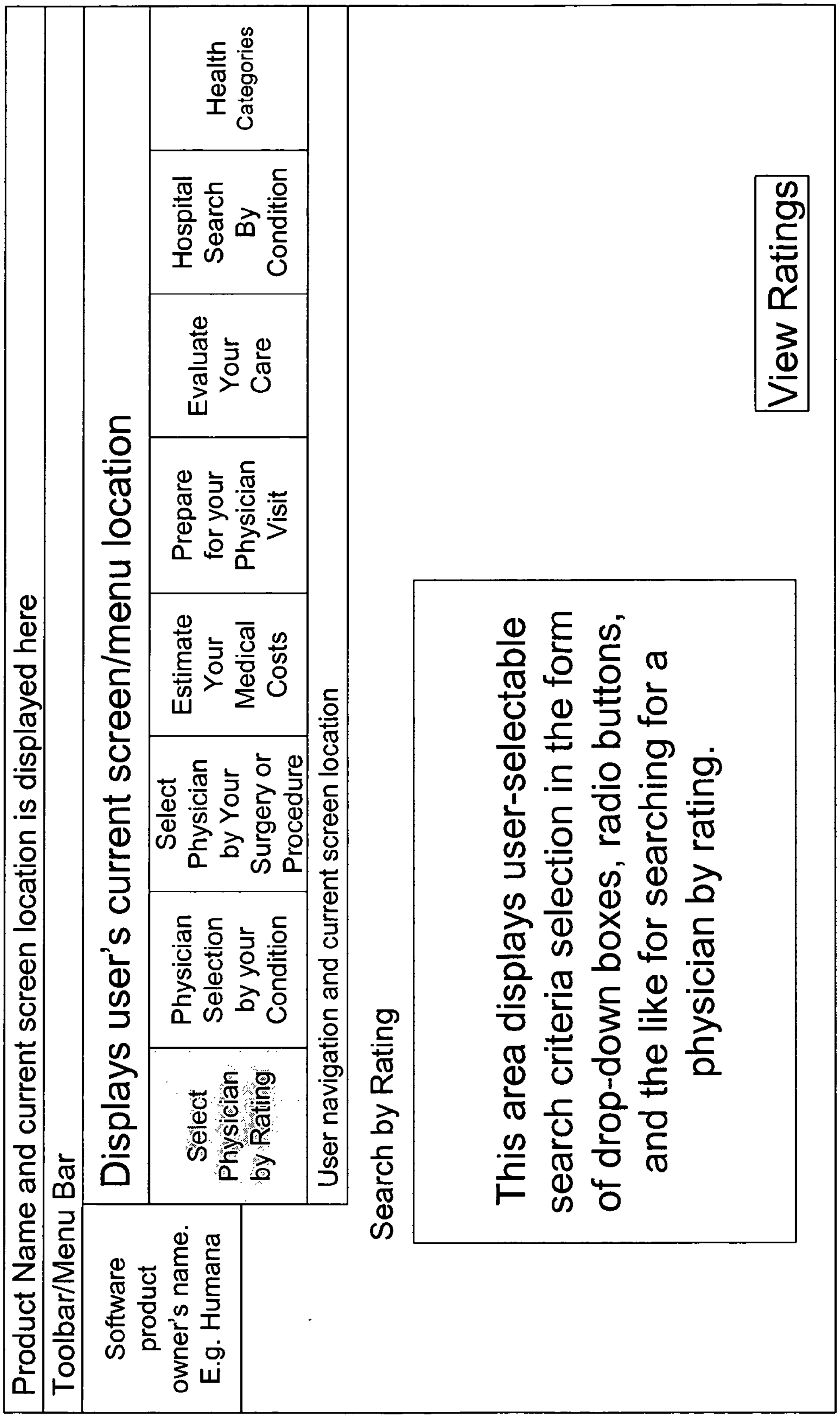

Fig. 2-1

| Software product owner's name. E.g. Humana | Displays user's current screen/menu location |
| | This area contains a set of user-selectable buttons for user navigation to primary screen locations per Figure 2-1 |

User navigation and current screen location

This area includes user-selectable scrolling lists of health issues, associated conditions, and condition descriptions This area displays user-selectable search criteria selection in the form of drop-down boxes, radio buttons, and the like so the user can search for a physician by condition

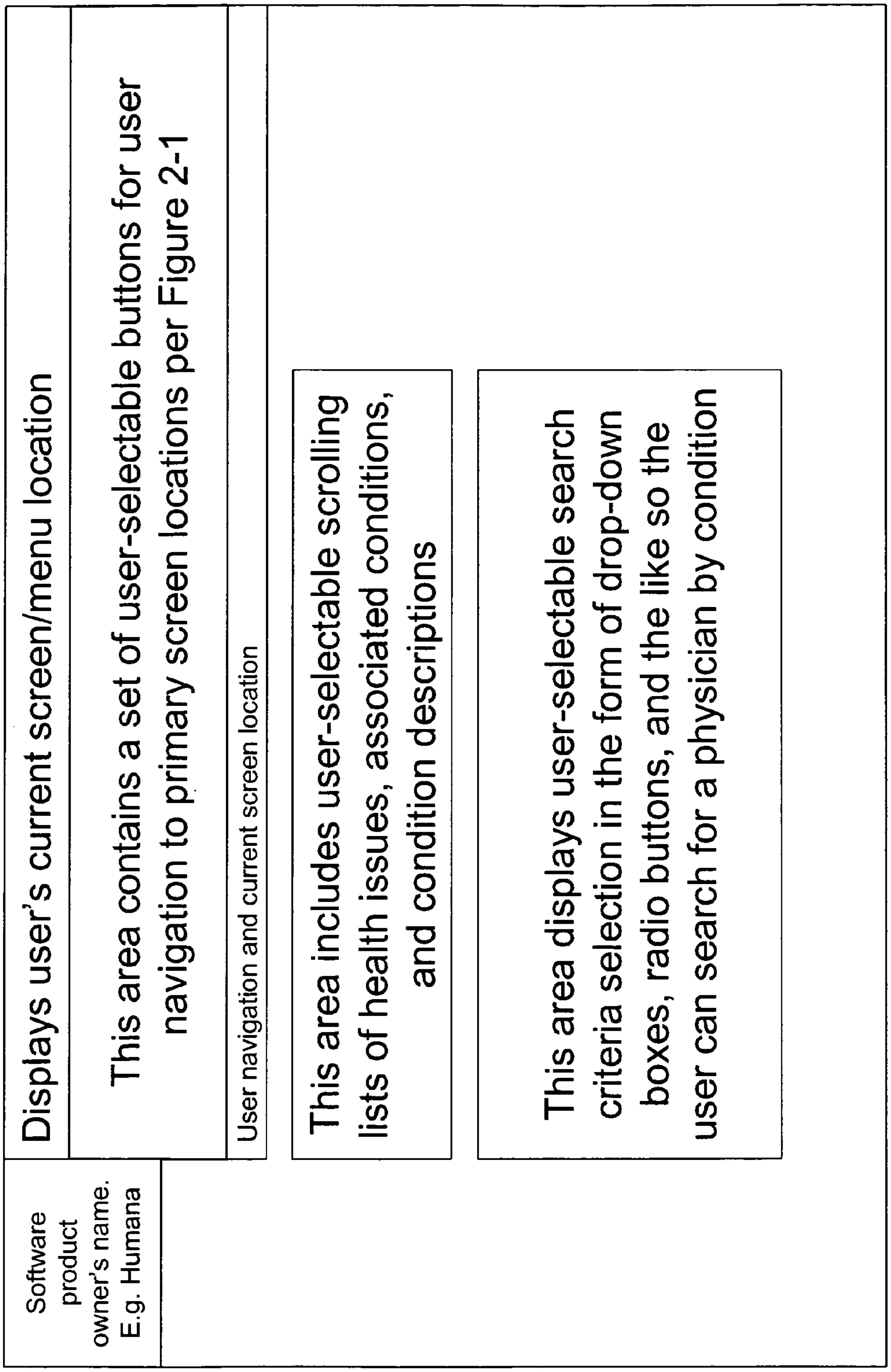

Fig. 2-2

| Product Name and current screen location is displayed | | |
|---|---|---|
| Toolbar/Menu Bar | | |
| Software product owner's name. E.g. Humana | Displays user's current screen/menu location | |
| | This area contains a set of user-selectable buttons for user navigation to screen to primary screen locations per Figure 2-1 | |
| | User navigation and current screen location | |
| | Displays current search criteria | |
| | Displays the ratings key | |
| | | Displays a spreadsheet list of the top specialties treating the user's condition based on user-selected criteria. |

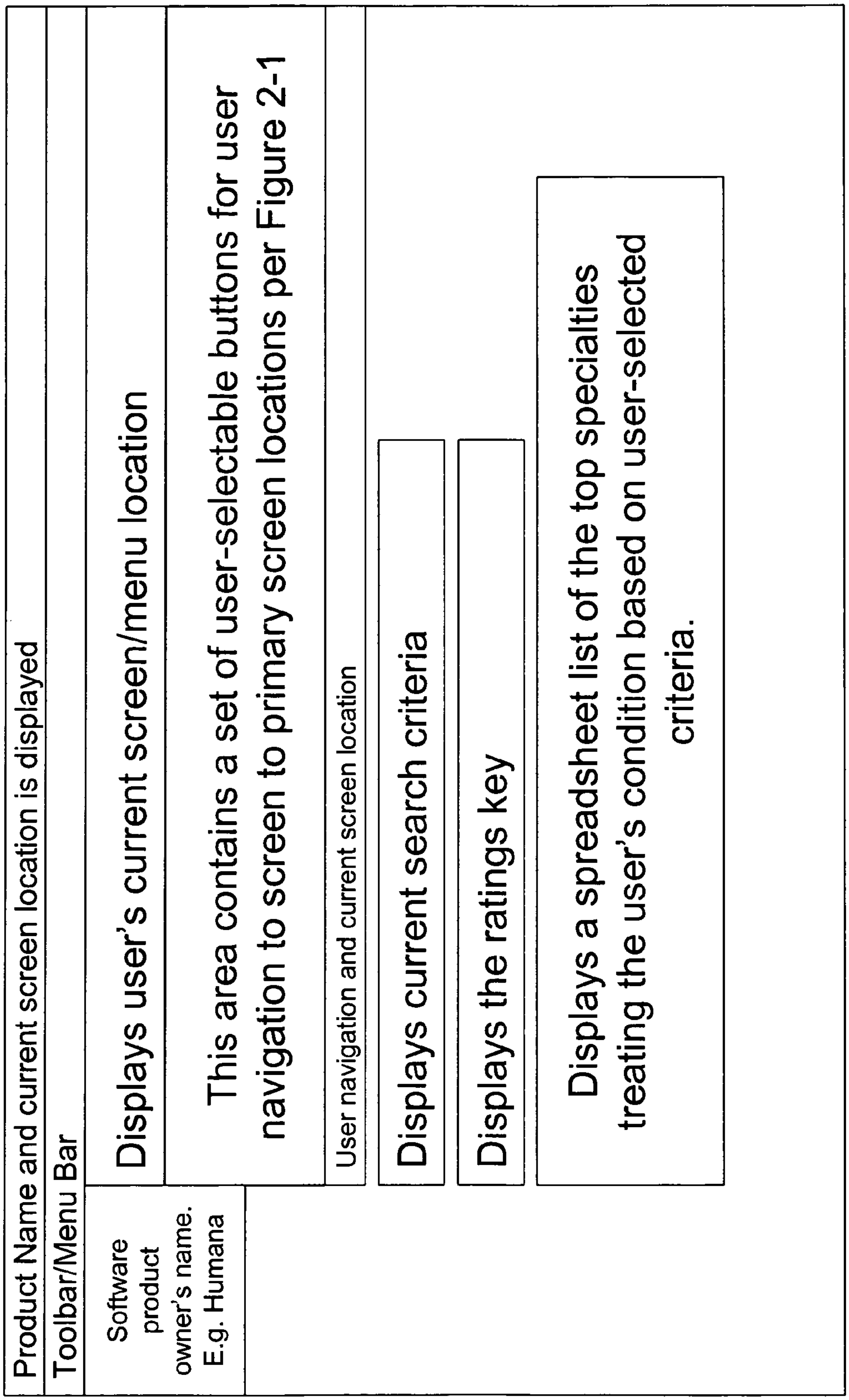

Fig. 2-3

| Product Name and current screen location is displayed | | | | |
|---|---|---|---|---|
| Software product owner's name. E.g. Humana | Displays user's current screen/menu location | | | |
| | This area contains a set of user-selectable buttons for user navigation to primary screen locations per Figure 2-1 | | | |
| | User navigation and current screen location | | | |
| | | Displays current search criteria | | Displays a spreadsheet of physicians capable of treating a user's selected medical condition and ratings in several categories. The list is adjustable by driving distance. |
| | | Displays the ratings key | | |

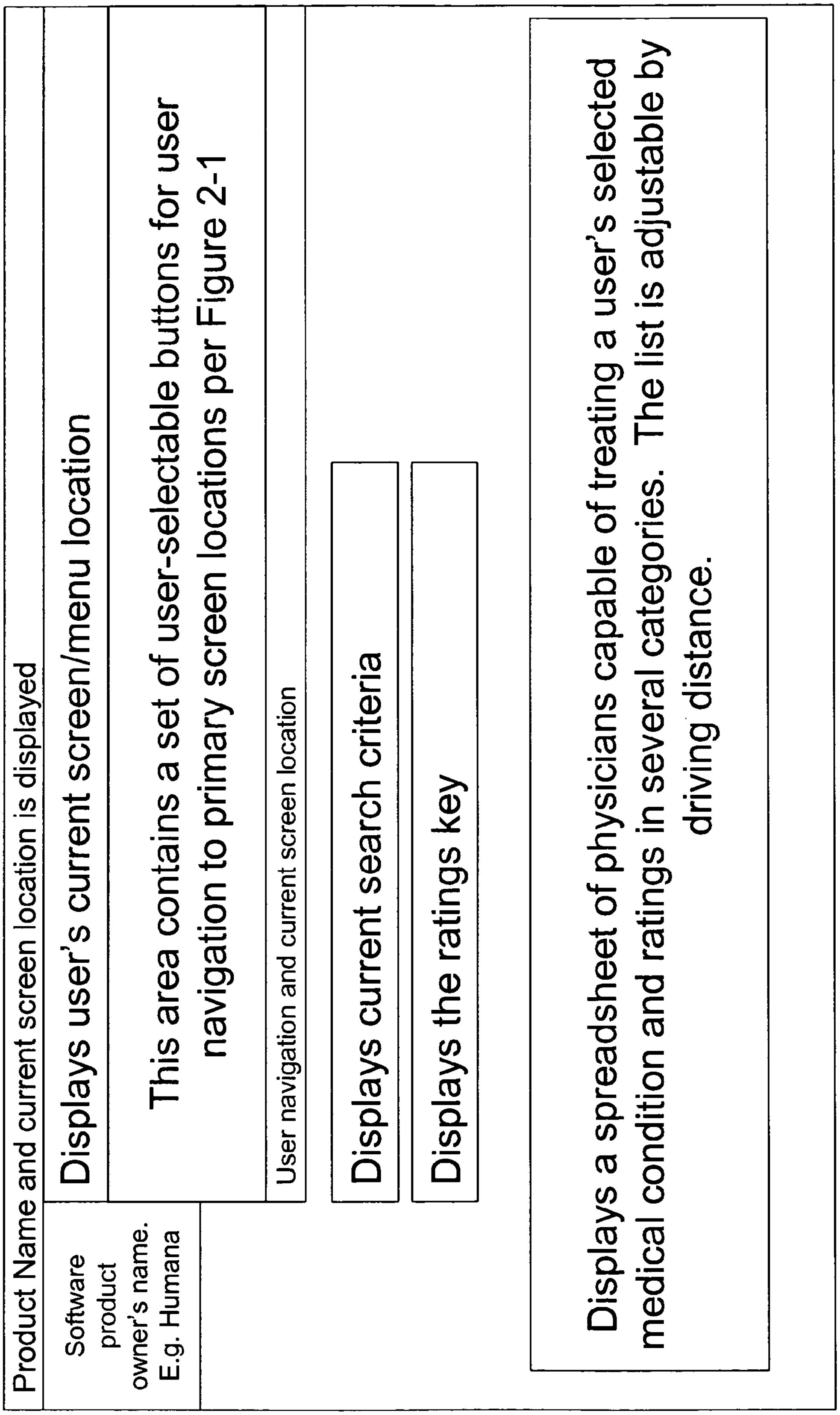

Fig. 2-4

| Product Name and current screen location is displayed |
|---|
| Toolbar/Menu Bar |

| Software product owner's name. E.g. Humana | Displays user's current screen/menu location |
| --- | --- |
| | This area contains a set of user-selectable buttons for user navigation to primary screen locations per Figure 2-1 |
| | User navigation and current screen location |
| | Displays current search criteria |
| | Displays the ratings key |

Displays the selected physician's demographic contact information with a link to obtain driving directions Displays physician and group practice ratings in a spreadsheet format

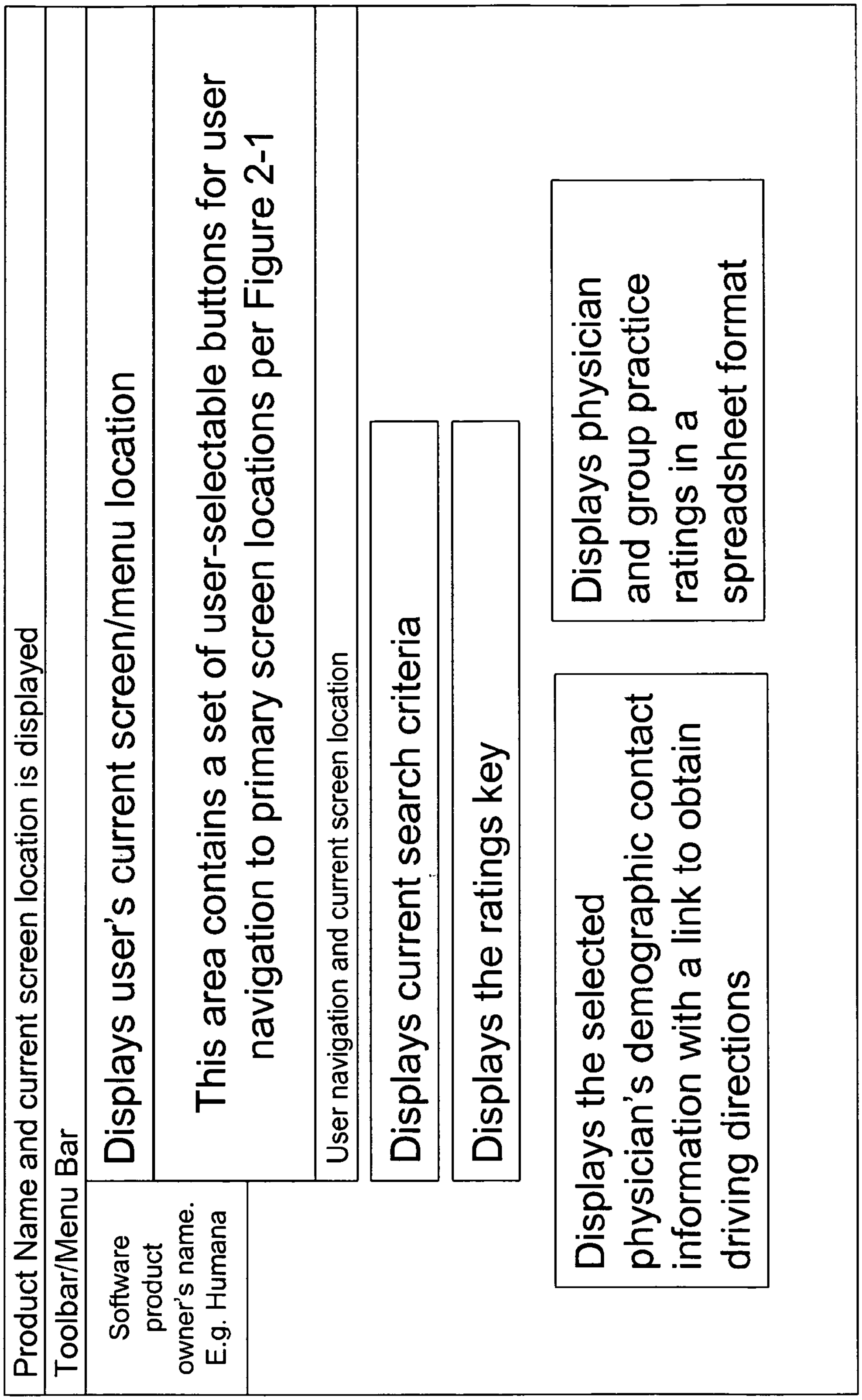

Fig. 2-5

| Product Name and current screen location is displayed | | |
|---|---|---|
| Toolbar/Menu Bar | | |
| Software product owner's name. E.g. Humana | Displays user's current screen/menu location | |
| | This area contains a set of user-selectable buttons for user navigation to primary screen locations per Figure 2-1 | |
| | User navigation and current screen location | |
| | Displays the current search criteria | |
| | Displays the ratings key | Displays physician clinical quality for the selected condition using the rating system in a spreadsheet format |
| | Displays the selected physician's demographic contact information with a link to obtain driving directions | |

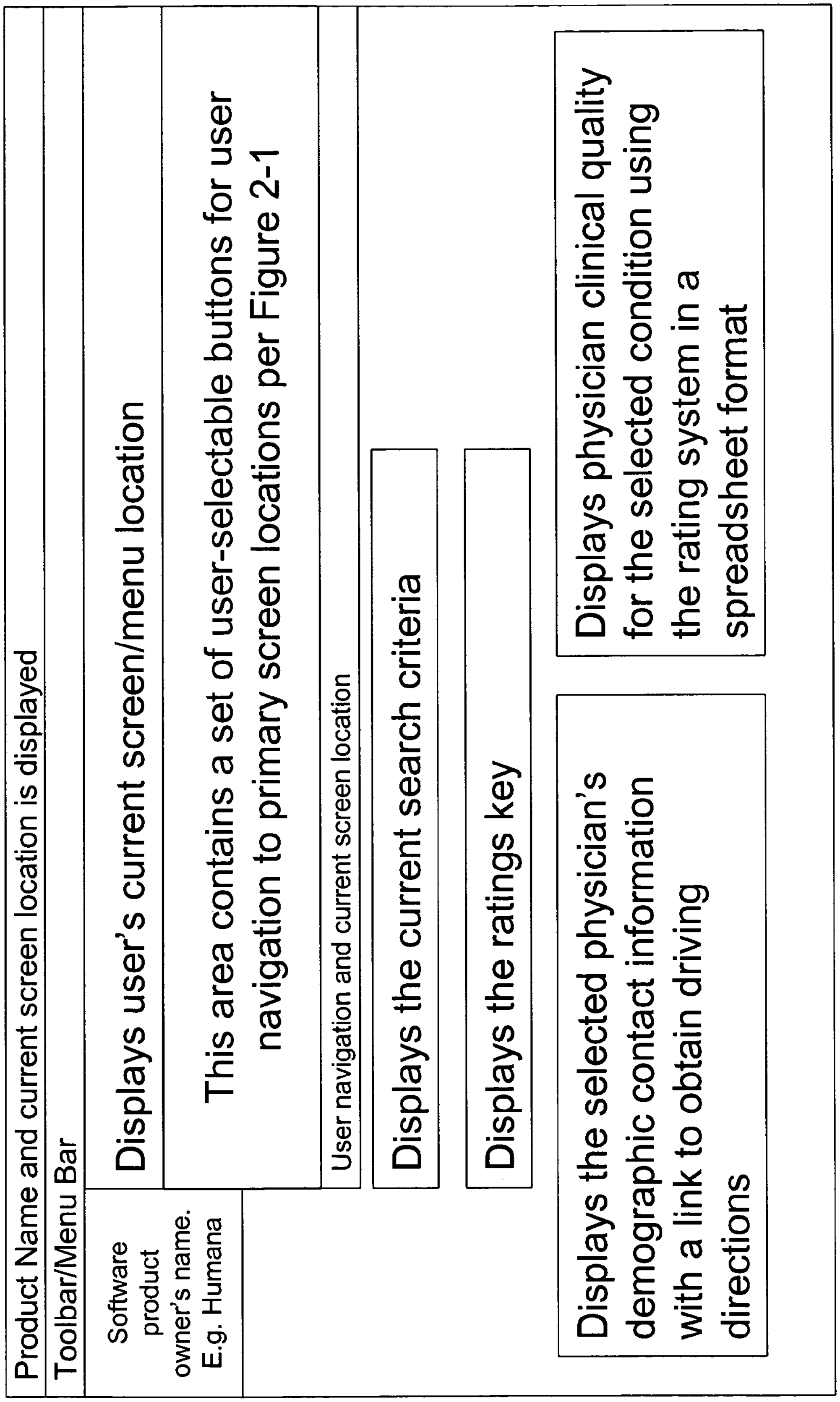

Fig. 2-6

| | |
|---|---|
| Product Name and current screen location is displayed | |
| Toolbar/Menu Bar | |
| Software product owner's name. E.g. Humana | Displays user's current screen/menu location |
| | This area contains a set of user-selectable buttons for user navigation to primary screen locations per Figure 2-1 |
| | User navigation and current screen location |
| | Displays the current search criteria |
| | Displays the ratings key |
| | Displays the selected physician's demographic contact information with a link to obtain driving directions |
| | Displays physician clinical quality for the selected condition in a spreadsheet format based on affiliations using the rating system |

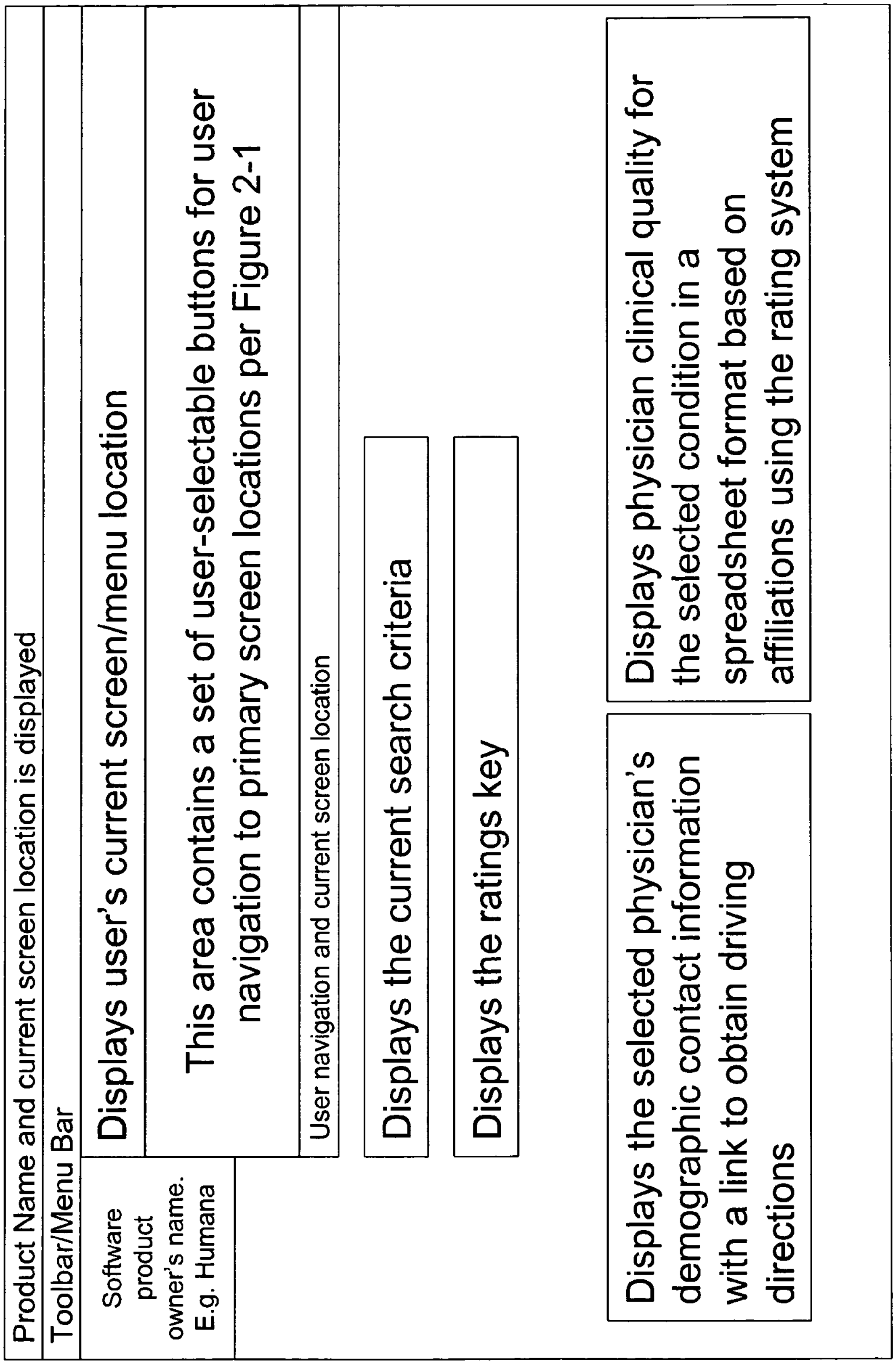

Fig. 2-7

| | |
|---|---|
| Product Name and current screen location is displayed here | |
| Toolbar/Menu Bar | |

| Software product owner's name. E.g. Humana | Displays user's current screen/menu location |
| --- | --- |
| | This area contains a set of user-selectable buttons for user navigation to primary screen locations per Figure 2-1 |
| | User navigation and current screen location |
| | Displays the current search criteria |
| | This area includes user-selectable scrolling lists of health issues, associated procedures, and procedure descriptions |

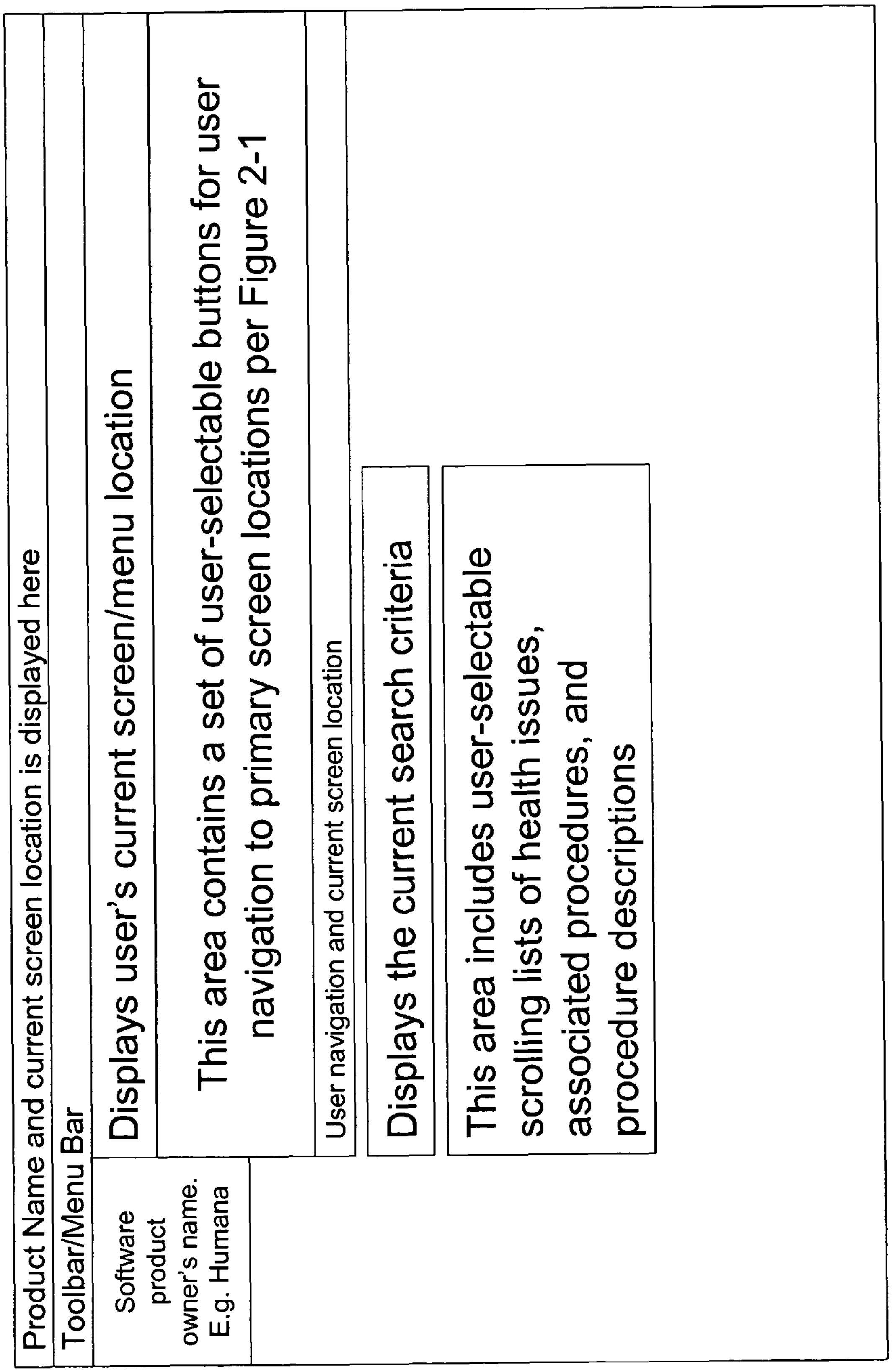

Fig. 2-8

| Product Name and current screen location is displayed here | | | |
|---|---|---|---|
| Toolbar/Menu Bar | | | |
| Software product owner's name. E.g. Humana | Displays user's current screen/menu location | | |
| | This area contains a set of user-selectable buttons for user navigation to primary screen locations per Figure 2-1 | | |
| | User navigation and current screen location | | |
| | | Displays the current search criteria | |
| | | Displays a list of physicians capable of treating a condition selected by the user in a spreadsheet form including cost data, statistical data, and information. The list is adjustable based on driving distance | |

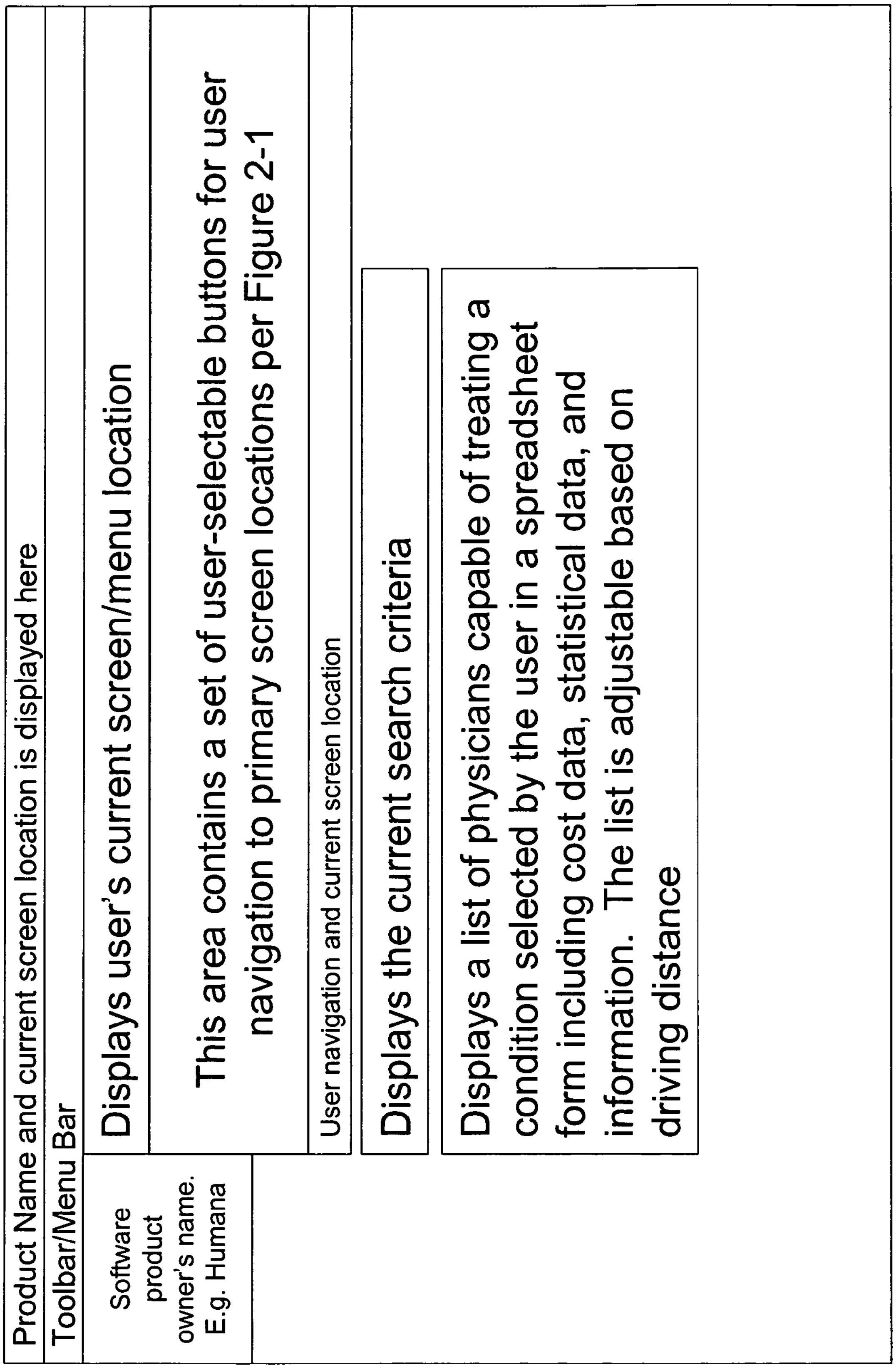

Fig. 2-9

| Product Name and current screen location is displayed here | |
|---|---|
| Toolbar/Menu Bar | |
| Software product owner's name. E.g. Humana | Displays user's current screen/menu location |
| | This area contains a set of user-selectable buttons for user navigation to primary screen locations per Figure 2-1 |
| | User navigation and current screen location |
| | Displays the current search criteria |
| | Displays user-selectable links to additional information |
| | Displays a list of physicians capable of treating a condition selected by the user in a spreadsheet form including cost data, statistical data, and information. The list is adjustable based on driving distance. The user can compare physicians by selecting the physicians to compare. |

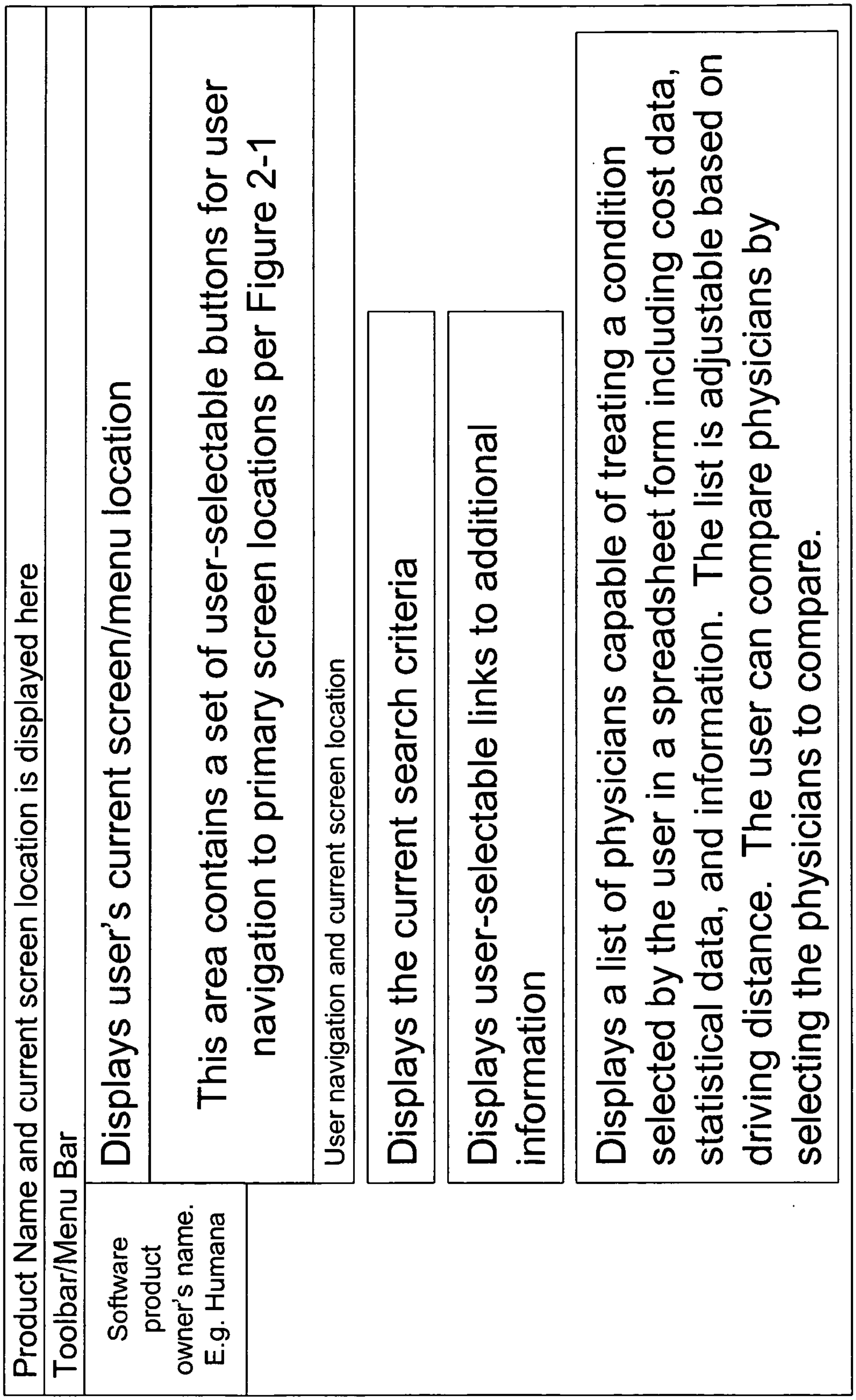

Fig. 2-10

| Product Name and current screen location is displayed here | | |
|---|---|---|
| Toolbar/Menu Bar | | |
| Software product owner's name. E.g. Humana | Displays user's current screen/menu location | |
| | This area contains a set of user-selectable buttons for user navigation to primary screen locations per Figure 2-1 | |
| | User navigation and current screen location | |
| | Displays the current search criteria | |
| | Displays user-selectable links to additional information | |
| | Displays a list of physicians capable of treating a condition selected by the user in a spreadsheet form including cost data, statistical data, and information. The list is adjustable based on driving distance. The user can compare physicians by selecting the physicians to compare. | |

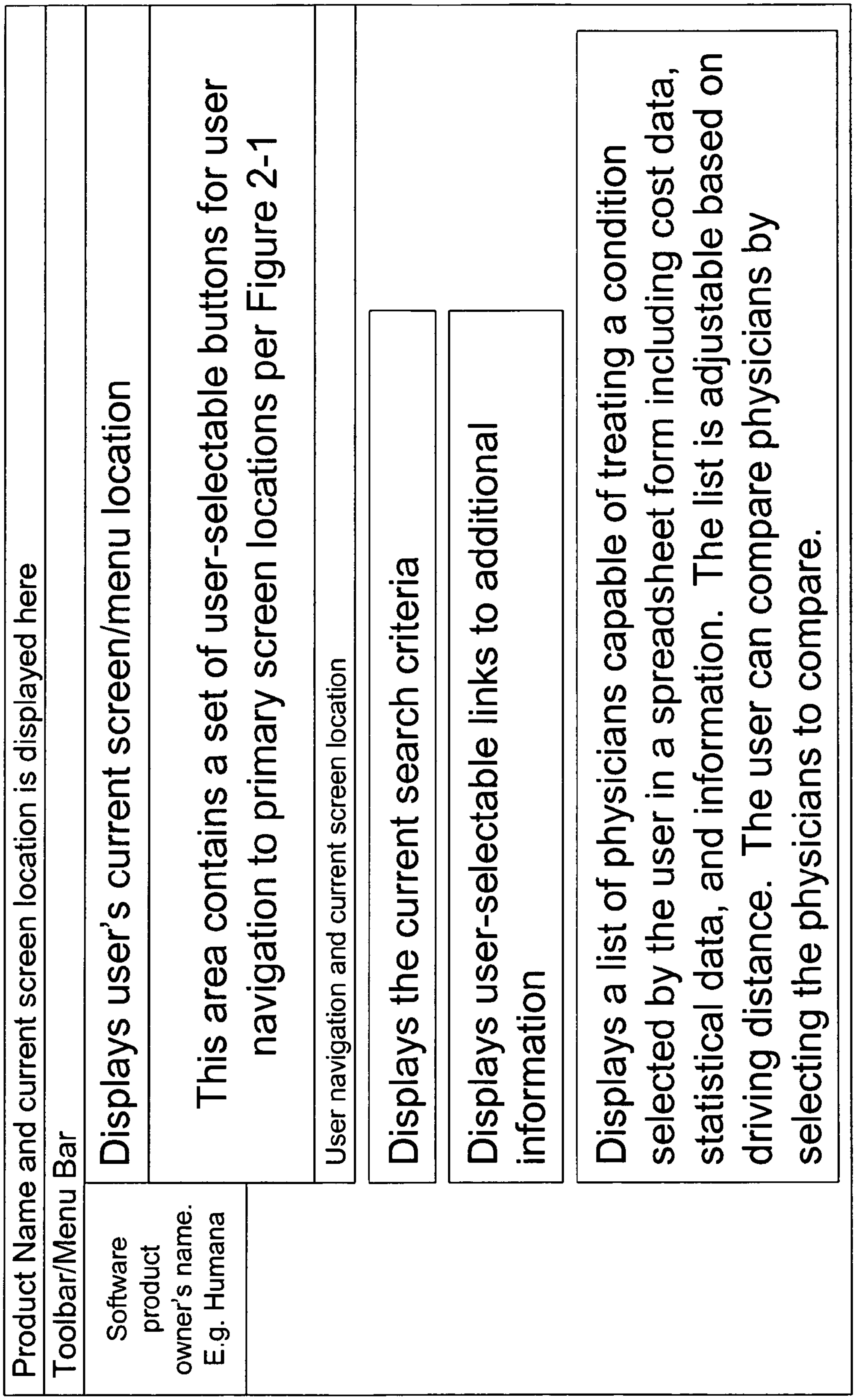

Fig. 2-11

| Product Name and current screen location is displayed here |
|---|
| Toolbar/Menu Bar |

| Software product owner's name. E.g. Humana | Displays user's current screen/menu location |
| --- | --- |
| | This area contains a set of user-selectable buttons for user navigation to primary screen locations per Figure 2-1 |
| | User navigation and current screen location |
| | Displays user-selectable links to information personalized by search criteria already entered by the user |

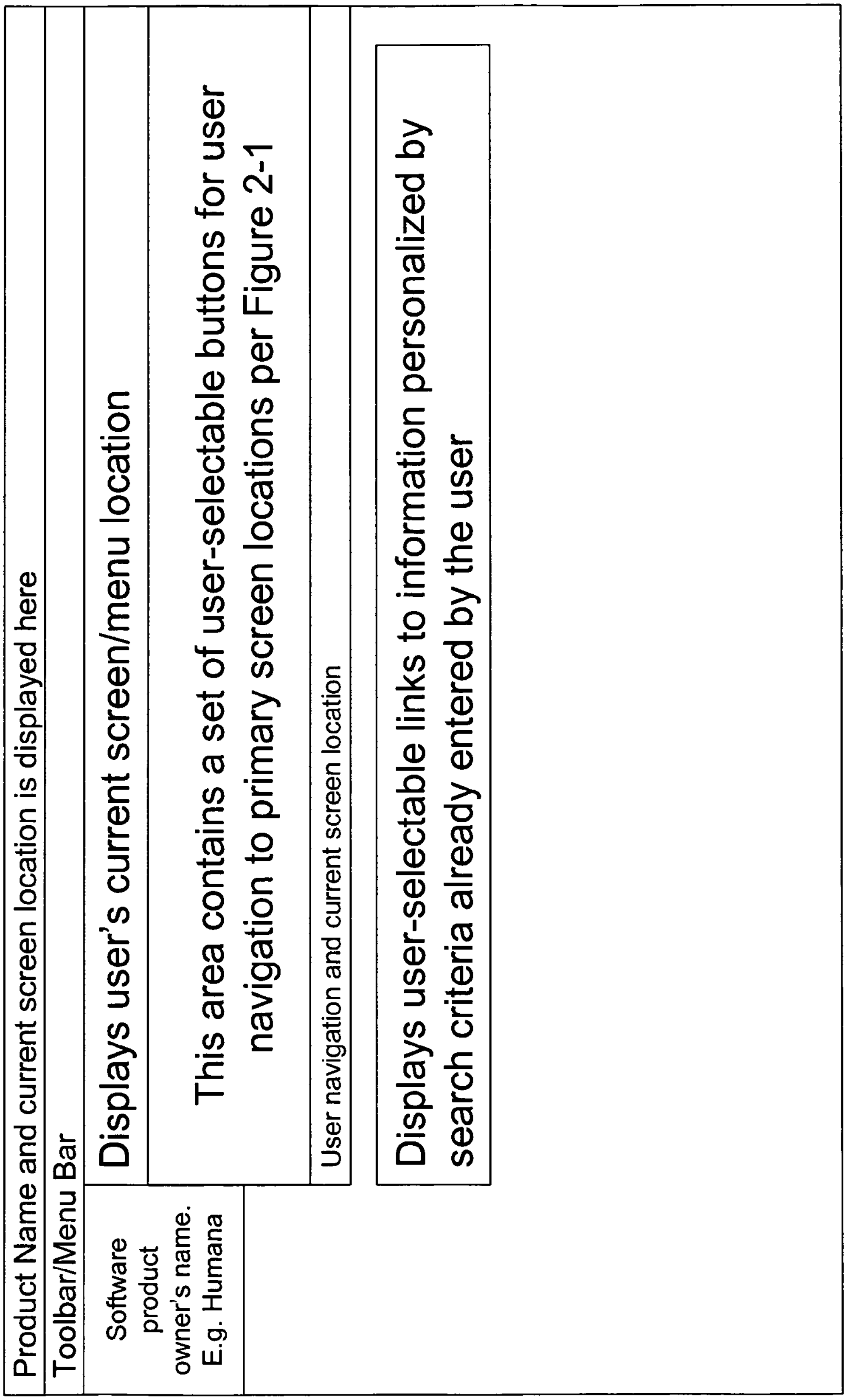

Fig. 2-12

| Product Name and current screen location is displayed here |  |  |
|---|---|---|
| Toolbar/Menu Bar |  |  |
| Software product owner's name. E.g. Humana | Displays user's current screen/menu location | Displays a set of controls are displayed that allow the user to question a physician, take a health risk survey, review their health summary, chat with a health coach, and contact the physician in several different ways |
|  | This area contains a set of user-selectable buttons for user navigation to primary screen locations per Figure 2-1 | |
|  | User navigation and current screen location | |
|  |  | The user can search health topics by way of a search box |

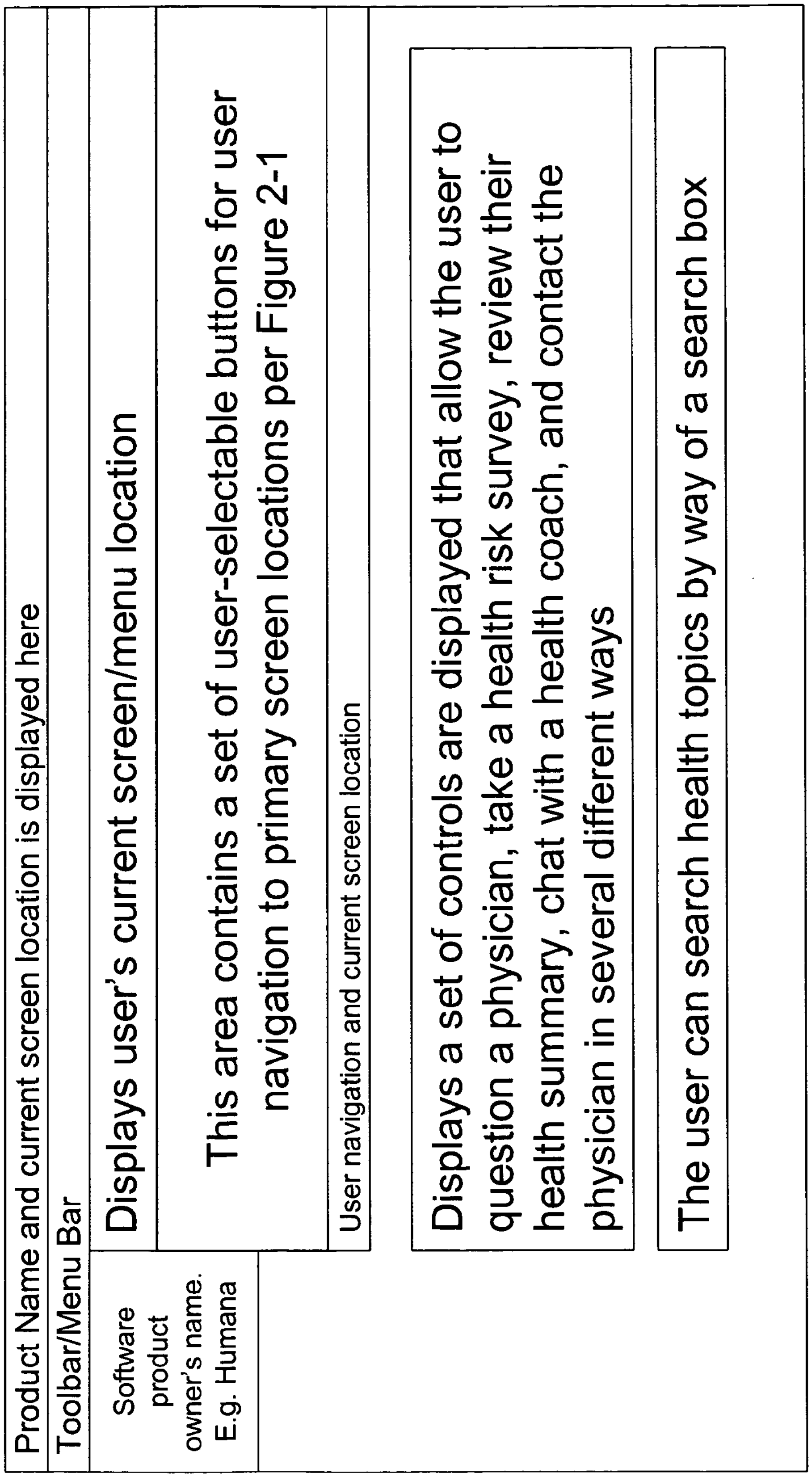

Fig. 2-13

| Product Name and current screen location is displayed here | | |
|---|---|---|
| Toolbar/Menu Bar | | |
| Software product owner's name. E.g. Humana | Displays user's current screen/menu location | |
| | This area contains a set of user-selectable buttons for user navigation to primary screen locations per Figure 2-1 | |
| | User navigation and current screen location | |
| | Display includes user-selectable scrolling lists of health issues, associated conditions, and condition descriptions | Display includes radio buttons for selection the severity of the condition selected above for computing the cost of treatment |

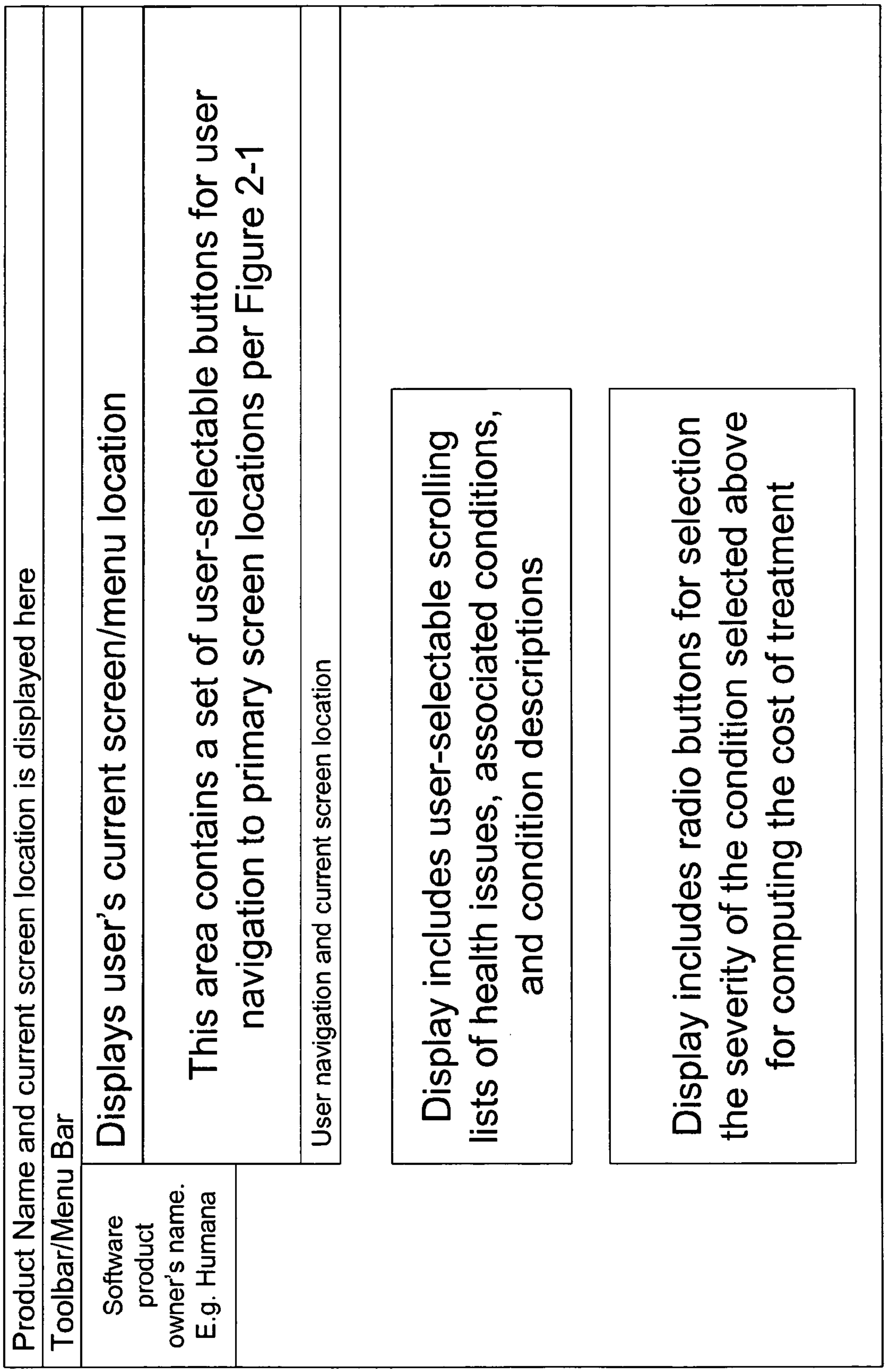

Fig. 2-14

| Product Name and current screen location is displayed here | | |
|---|---|---|
| Toolbar/Menu Bar | | |
| Software product owner's name. E.g. Humana | Displays user's current screen/menu location | |
| | This area contains a set of user-selectable buttons for user navigation to primary screen locations per Figure 2-1 | |
| | User navigation and current screen location | |
| | Displays the current search criteria | |
| | User-selectable links to additional information | |
| | Displays costs for treatment broken down by type of service. | |
| | Displays radio buttons for user to change severity of the condition being cost analyzed | |

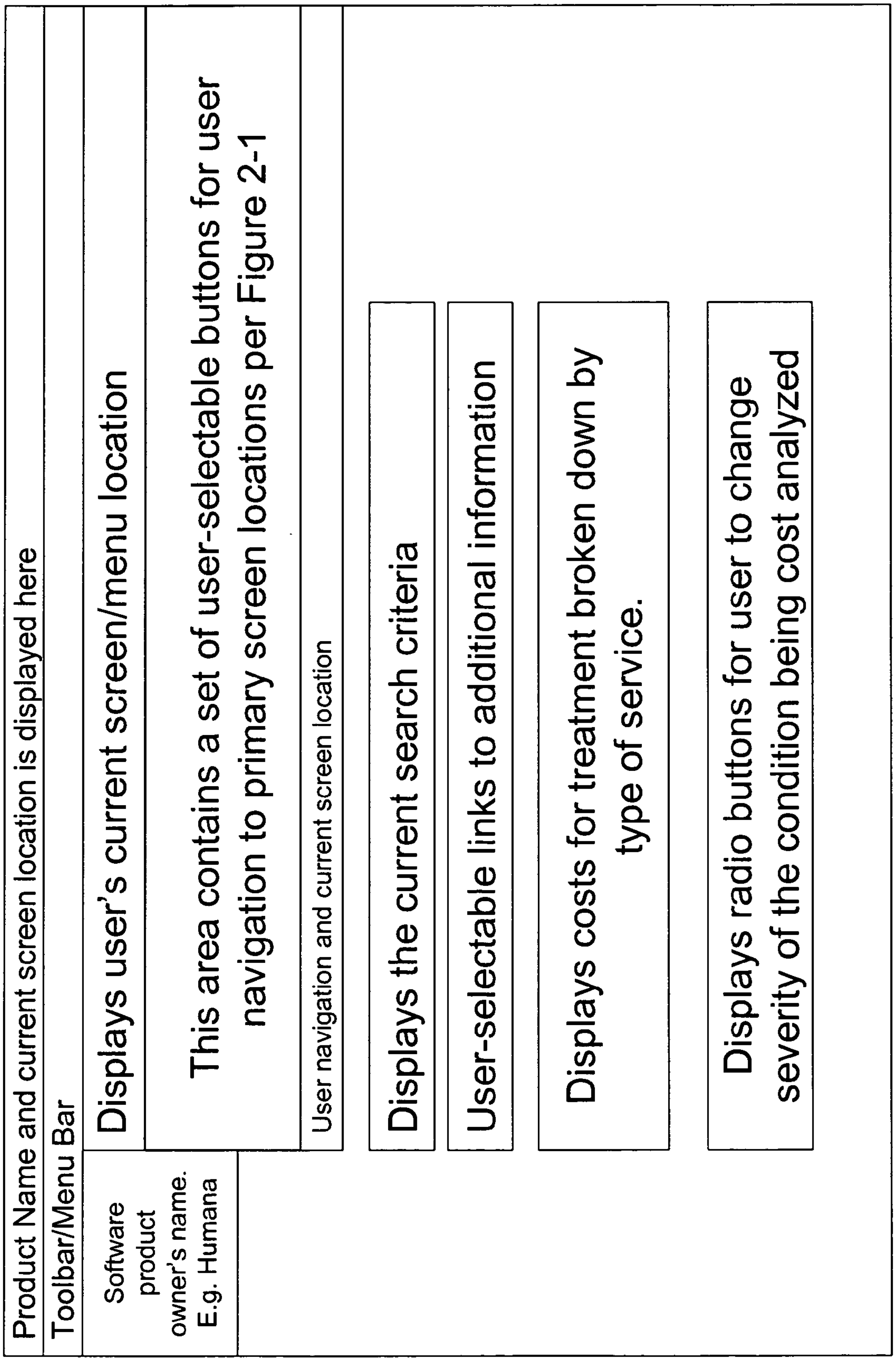

Fig. 2-15

DOCTOR PERFORMANCE EVALUATION TOOL FOR CONSUMERS

CROSS-REFERENCE TO RELATED APPLICATIONS

This application claims priority of the following applications, each hereby incorporated by reference as if fully set forth herein.

U.S. patent application Ser. No. 11/192,999, filed Jul. 29, 2005, in the names of Geoffrey BAKER and Pamela ROLLINS, titled "Physician Cost and Quality Evaluation Tool for Consumers".

U.S. provisional patent application No. 60/592,283, filed Jul. 29, 2004, in the name of Geoffrey BAKER, titled "Physician Cost and Quality Evaluation Tool for Consumers".

BACKGROUND OF THE INVENTION

1. Field of the Invention

The invention relates to a doctor performance evaluation tool.

2. Related Art

With the transfer of higher medical costs and premium payroll contributions for health benefits to consumers, payers of medical expenses (including insurance companies and employers who provide insurance benefits to their employees) must now provide more information about the cost of treatment and quality of care associated with such treatment, and other aspects of the medical experience, to patients (consumers, employees and their family dependents). Those payers (herein sometimes called "users") include the actual consumers of medical care (individuals, their parents or guardians, employees and their dependents) and the insurers of their medical costs (including employers, insurance companies, and government agencies). Many new health benefit plans make employees responsible for "first dollar" healthcare coverage costs (i.e., the employee pays for health expenses out-of-pocket until some benefit limit (deductible) when insurance benefits pay for the cost. These benefit plans can be made more affordable by rewarding consumers who select medical providers that deliver the most cost-effective high quality healthcare. In many cases, patients themselves have significant information about their specific healthcare needs and the types of medical care and providers needed for their treatment. Patients could thus significantly reduce their healthcare coverage costs if only they had adequate information about the specific cost of treatment and quality of care of their potential providers (i.e., doctors, hospitals, other health care professionals) for a specific condition, surgery or procedure.

Currently available information on the cost and quality of services provided by individual doctors is generally minimal at best, aggregated to be of little value, and often merely anecdotal (based on incomplete samples of self-reported, patient satisfaction surveys). Provider directories from insurance companies that help consumers select individual doctors generally exclude any such information on provider cost and quality. If insurance companies publish such performance results in directories on providers, such actual "performance scorecards" are often aggregated at the group practice level and not on the individual doctor level where the patient has a personal relationship. In addition, cost information about patient treatment is often aggregated and does not identify which providers are most cost-effective for surgery or for treating that patient's specific condition. Neither of these approaches provides users with the level of detail necessary to make choices that can minimize cost while maintaining quality, or even select providers based on other criteria important to them, such providers who can treat their condition, providers who have electronic medical records that can check for adverse drug interactions, ease of service or listening skills. Some known individual provider ratings, for example those provided by the NCQA (National Committee on Quality Assurance) provide some guidance to healthcare consumers on treatment of diabetes or heart conditions, but do not provide adequate or detailed enough information for selecting any particular medical provider based on individual provider quality or the user's actual medical condition, or specific treatment need.

Even when users do have access to performance scorecards for individual doctors, known measures of performance relate only to general capabilities of each particular doctor, and do not give useful information regarding capabilities of any particular doctor with regard to a specific healthcare need (such as the patient's medical condition, surgical or procedure need). Although the specialty in which the particular doctor practices, or the particular hospital department in which the doctor practices, might provide very rough information, the information is far too general to allow users to make adequately informed decisions about provider selection, particularly when users have to pay significant out of pocket monies for such health care services.

This problem is particularly acute when the user is looking for doctors that can best treat the user's particular medical condition, particular surgical need, particular medical history, or user's particular demographic profile. For example, an overweight male patient in his 50's with a family medical history of coronary disease might seek out a provider with best capabilities at coronary heart disease and its related medical conditions, while a newly married female patient in her 20's might seek out a provider with best capabilities at pregnancy and family issues. The latter might even specifically wish to have a female doctor. A user who already has a specific known medical condition, whether very specialized (say, allergy), or not (say, diabetes), or having both non-physical and physical components (say, psychopharmacology), will almost certainly wish to select a medical provider with best capabilities in that known medical condition and similar medical conditions. In known systems and provider directories, information about providers is limited to each medical provider's certifications, credentials, malpractice history, service locations, or general practice areas. While this does give the user some information about the general class of medical conditions that medical provider is capable of treating, it has the drawback of failing to provide specific information regarding the medical provider's actual record of prevention and treatment of the user's specific medical problems (whether current or anticipated).

Even where there is an attempt to measure individual doctor performance, current models do not adequately serve the user in providing unbiased and statistically valid measures. Disregarding their possible bias and statistical invalidity, the measures that do exist are not representative of the particular medical conditions and patient population diagnosed and treated by those medical providers. Current performance measures generally focus on a few aspects of the medical provider's practice, but do not reveal enough information to adequately judge the entire range or scope of the medical provider's practice across different patient panels and patient treatments, including relatively healthy patients, occasionally sick patients, and chronically ill patients. This has the effect that measured performance for distinct medical providers could vary substantially in response to their differing patient populations, rather than in response to an individual user's needs.

For example, one known method, a "patient weighted" measurement, is responsive, for each medical provider, to an average score of their performance across a set of intervention opportunities. Each performance measure represents a component of that total average score. The total average score is weighted by the volume of intervention opportunities. This method has the substantial drawback since each medical provider's score is most heavily weighted toward the component of that average in which they treated the largest number of patients. Those measures with a smaller volume of intervention opportunities which are equally important as high volume intervention opportunities do not receive equal weight. This drawback is substantial and creates biased results because, among other reasons, certain measures of quality may apply to patients with a first type of condition (e.g., preventative care of the heart—cholesterol screenings) where the patient sample size per doctor is very large, but are substantially valuable in measuring the same doctor for a second type of condition (e.g., patients with coronary artery disease) where the patient sample size is small.

SUMMARY OF THE INVENTION

The invention includes methods and systems, including techniques for presenting information to patients that yield easily understood, yet statistically valid, rankings, in multiple scoring domains, in response to those patients' desire to find or compare medical providers associated with their particular medical condition or treatment needs, as well as other criteria.

In a first aspect of the invention, the system is able, from data on medical providers that is relatively limited, to rank order medical providers within a specific category (such as "all cardiologists") based on performance across a measure or several measures, and to assign bucket rankings to groups of those medical providers, while assuring that those bucket rankings are statistically different. For example, a $1^{st}$ group of medical providers might receive a bucket ranking of 1 (such as represented by 1 star "*"), a $2^{nd}$ group of medical providers might receive a bucket ranking of 2 (such as represented by 2 stars "**"), and the like. The system preferably uses 3-4 bucket rankings, but the actual number of bucket rankings used in any particular embodiment may be more or fewer. The system is able to make statistically valid differentiations between medical providers irrespective of number of measurements available.

In a second aspect of the invention, the system provides a UI (user interface), by which a patient can (1) specify one or more medical conditions or treatments, and possibly other options, (2) search for medical providers appropriate to those conditions, and order them by bucket ranking in the patients' choice of scoring domain, and (3) obtain more detailed information with regard to those selected medical conditions or medical treatments (e.g., surgeries or other procedures), for selected medical providers.

In preferred embodiments, the UI might be presented using an internet connection such as a web site (but alternatively might be presented at a specialized location, such as a patient's home or doctor's office), with information being retained (at the patients' option) regarding the patients' medical history, the patients' preferences, and the patients' health insurance plan benefit coverage.

In preferred embodiments, the UI might also include (1) selection of particular medical conditions, either directly, by reference to a medical category, or with assistance of a health coach, (2) selection of particular medical surgeries or procedures, by reference to a medical category, or with assistance of a health coach, (3) selection of one or more score domains in preferential order (i.e., Clinical Quality, Affordability, Patient Experience, Service Quality, and Clinical Systems), and (4) possible selection based on additional requirements, such as:

- distance from patient's location;
- preferred gender for an individual medical provider;
- whether the selected medical provider uses an electronic medical record or "patient registry";

In preferred embodiments, medical providers having a "patient registry" include those who, among other things,

- support patient outreach
- track conditions and the health status of individual patients and population of patients using clinical and other measures
- generate reports identifying patients assigned to a responsible provider, and
- generate reports identifying individual patients requiring follow-up or other possible gaps in care.

However, in the context of the invention, there is no particular requirement that a medical provider have each and every one of these features before being identified as having a "patient registry." In alternative embodiments, the system may identify those medical providers who perform a significant fraction of these functions as having patient registries, or may rank the medical provider in terms of the completeness and quality of its patient registry.

- whether the selected medical provider performs electronic prescribing;
- whether the selected medical provider provides health education materials;
- whether the selected medical provider performs health risk assessments;
- whether the selected medical provider is accepting new patients; or
- whether the selected medical provider accepts the patient's benefit plan and insurance coverage.

In preferred embodiments, the UI might also include presentation of those medical providers in an order responsive to the patient's stated preferences, responsive to rankings in the patients' preferred score domains, and responsive to possible additional criteria imposed by the patient. The UI might also provide the capabilities for the patient to obtain more detail about selected medical providers, or for the patient to compare multiple medical providers, both without the patient having to know anything about how those rankings are prepared, anything about medical specialties, or anything about what specific medical conditions the patient might have.

Enabling Technology

After reading this application, those skilled in the art would recognize that it provides an enabling technology for a wide variety of novel and non-obvious methods and systems. Some of these new methods and systems include the following:

- Healthcare users can select medical providers with knowledge of the user's own medical conditions and history, increasing their ability to obtain healthcare at lower cost without sacrificing quality, or at the same cost with better quality, or some combination thereof.
- As part of this new technique, healthcare users can be guided to appropriate doctors in response to one or more of the following search criteria: 1.) Their known medical conditions and history, 2.) Their known medical surgeries or procedures needed, 3.) a set of diagnosis or symptom evaluation tools, and the like.

- Healthcare users can also be better prepared for their appointments with medical providers because this new technique can provide them with and combination of: 1.) one or more of a set of questions to ask, 2.) a set of symptoms to describe, 3.) a set of tests or other evidence to provide (to the appropriate medical provider), and the like.
- Healthcare users can select medical providers with knowledge of which services they consider essential and their benefits covered by insurance which services they consider optional, with the same or similar advantageous effects.
- As part of this new technique, healthcare users can be provided with a UI allowing relatively easy navigation of ratings for medical providers, including detailed information (if requested) on several scoring domains such as an appropriate medical provider's affordability (efficiency), quality, service, and the like. As described below, in preferred embodiments the UI presents the composite score of multiple individual measures, using an intuitive "bucket ranking" representation of percentile scores, such as 1 star "*" to 3 stars "***".
- Employers and insurers can reward healthcare users who select medical providers delivering quality healthcare services at reasonable cost, thereby reducing costs to these users without sacrificing benefits and health insurance coverage.
- As part of this new technique, insurers can provide defensible and statistically valid measurements of doctor quality and cost of care, both with regard to national norms, specialty norms, other peer group norms, norms related to known patient risk, norms based on an absolute threshold (e.g., $90^{th}$ percentile), ranges of performance (i.e., minimum $30^{th}$ percentile through a maximum $80^{th}$ percentile), and the like. This will be particularly useful when multiple medical providers across several specialties are working with the same patients with known, multiple, and possibly severe conditions. This is also useful for large insurance companies that want to compare the performance of medical providers in one region with providers in other regions while using the same measurement standards for quality, cost, and other criteria.
- Medical providers who offer affordable quality healthcare services can more readily disseminate that information to prospective patients and reimbursing entities, enabling those medical providers to advance to their highest and best positions as professionals in the marketplace.
- Medical providers can reduce their practice variation (with the effect of improving the quality and reliability of their care to patients) by following up with patients who are non-compliant with evidence-based quality of care measures.
- As part of this new technique, providers can look up actionable information required to improve their composite quality and cost scores. This includes searching for the patients in their quality measure scores (patient populations in the numerator and denominator) who have not received required services and who need to be contacted for a doctor office visit, preventative test or other required treatment. This will be particularly useful for continuous quality improvement.
- As a part of this new technique, insurers can allow providers to identify exceptions and to improve data quality when patients in a doctor's measure score (numerator and denominator) are based on patients that are not under the direct care of that doctor (i.e., patient assignment to a responsible provider may require correction). This has the advantage of increasing reliability of scores, creating an appropriate validation process and audit trail, and finally of reducing false positive rates.
- Healthcare users and medical providers can combine to provide healthcare benefits and services more effectively, more efficiently, more transparently, and more wisely, with the effect that the national provision of healthcare services is improved.

After reading this application, those skilled in the art would recognize that the invention also provides other and further novel and non-obvious methods and systems.

INCORPORATED DISCLOSURE

Each of the following documents is hereby incorporated by reference, as if fully set forth herein.

- U.S. provisional patent application No. 60/592,283, filed Jul. 29, 2004, in the name of Geoffrey BAKER, titled "Physician Cost and Quality Evaluation Tool for Consumers".
- U.S. patent application Ser. No. 11/192,999, filed Jul. 29, 2005, in the name of Geoffrey BAKER, titled "Physician Cost and Quality Evaluation Tool for Consumers".

These documents are sometimes referred to herein as the "incorporated disclosure".

BRIEF DESCRIPTION OF THE DRAWINGS

FIG. 2 (including FIG. 2-1 through FIG. 2-21, collectively referred to herein as FIG. 2) shows a set of screenshots and navigation flowcharts for a doctor performance evaluation tool.

FIG. 2-1 illustrates a screen shot for searching by physician rating.

FIG. 2-2 illustrates a screen shot for searching by medical condition.

FIG. 2-3 illustrates a screen shot for top specialties for treating a medical condition.

FIG. 2-4 illustrates a screen shot of a list of physicians treating a selected medical condition.

FIG. 2-5 illustrates a screen shot of a physician profile.

FIG. 2-6 illustrates a screen shot of a physician profile with a clinical quality indicator.

FIG. 2-7 illustrates a screen shot of a physician profile with a hospital affiliations indicator.

FIG. 2-8 illustrates a screen shot of surgery/procedure information.

FIG. 2-9 illustrates a screen shot of surgery/procedure costs and benefits in-formation by physician.

FIG. 2-10 illustrates a screen shot of physician comparisons information.

FIG. 2-11 illustrates a screen shot including a pointer to health education information.

FIG. 2-12 illustrates a screen shot of a personalized health education.

FIG. 2-13 illustrates a screen shot of a preparation for visit.

FIG. 2-14 illustrates a screen shot of patient cost estimation.

FIG. 2-15 illustrates a screen shot of finding a physician based on cost estimates.

FIG. 2-16 illustrates a flow diagram of navigation functions performed by the system.

FIG. 2-17 illustrates a flow diagram of user selection of a service provider based on a set of criteria related to provider rating.

FIG. 2-18 illustrates a flow diagram of user selection of a service provider based on a set of criteria related to patient condition.

FIG. 2-19 illustrates a flow diagram of user selection of a service provider based on a set of criteria related to the type of surgery or procedure to be performed.

FIG. 2-20 illustrates a flow diagram of treatment planning.

FIG. 2-21 illustrates a flow diagram for estimating costs and finding a physician.

FIG. 3 shows a process flow diagram of a method including determining a composite score for measures of quality for medical providers.

DETAILED DESCRIPTION OF PREFERRED EMBODIMENTS

Figure 1:
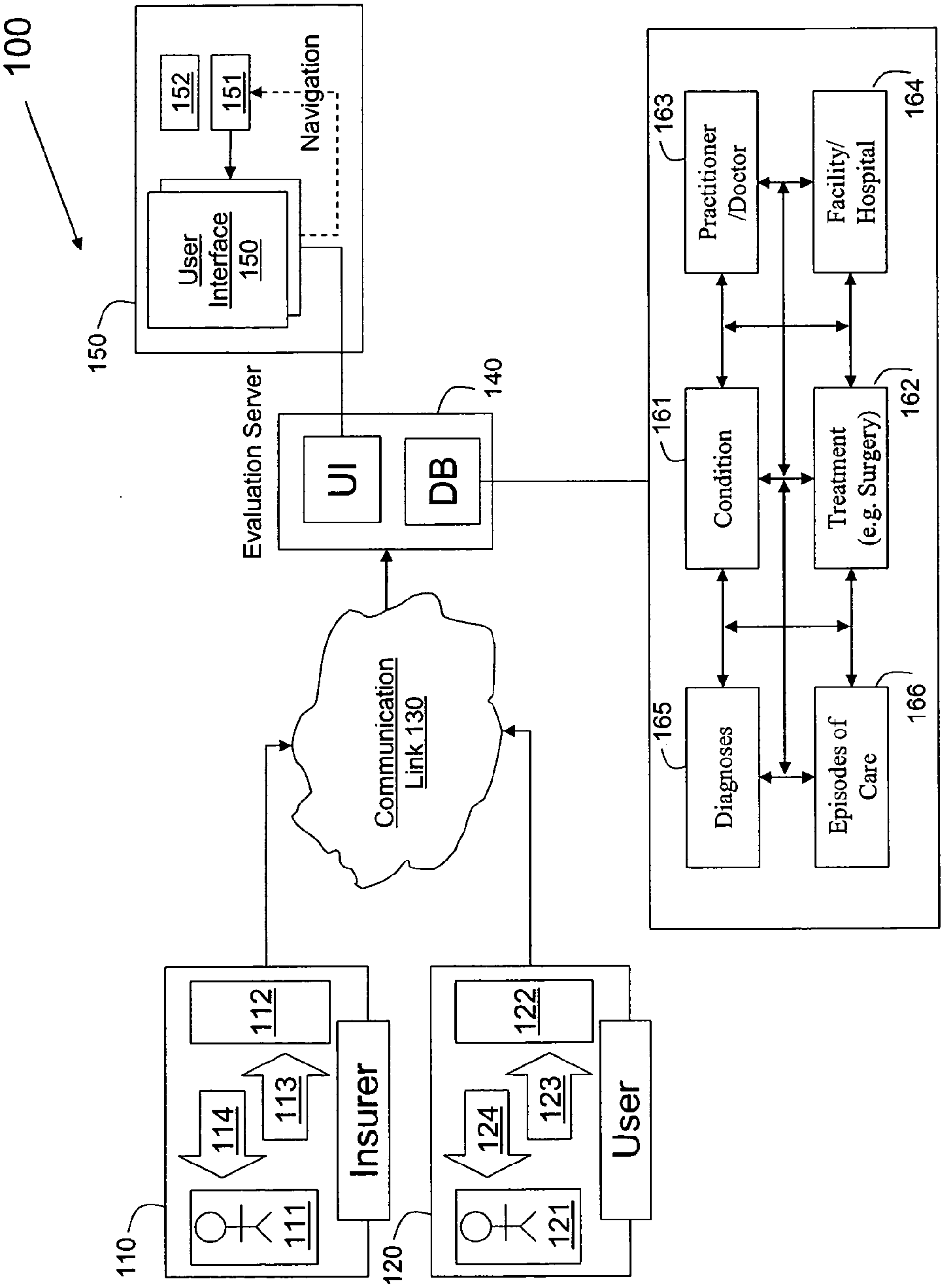
FIG. 1 shows a block diagram of a system including a doctor performance evaluation tool.

Although preferred method steps, system elements, data structures, and the like, are described herein, those skilled in the art will recognize that these are intended to describe the invention in its broadest form, and are not intended to be limiting in any way. The invention is sufficiently broad to include other and further method steps, system elements, data structures, and the like. Those skilled in the art will recognize these as workable without undue experimentation or further invention, and as within the concept, scope, and spirit of the invention.

DEFINITIONS

The general meaning of each of these following terms is intended to be illustrative and in no way limiting.

The term "user", and the like, generally refers to any patient, any dependent, patient's agent (such as a parent or guardian), or other person directing healthcare services for the patient, or any insurer of the patient's healthcare costs, such as an employer, insurance company, or government agency, or other entity responsible for healthcare costs for the patient (including the patient themselves).

The phrase "medical provider", and the like, generally refers to any person, group of people, or facility, providing or capable of providing healthcare services of any kind, or any kind of services appurtenant to healthcare. This phrase includes any "medical practitioner", as described below, and any "medical facility", as described below.

The phrase "medical practitioner", and the like, generally refers to any person, group of people, or organization of people, providing or capable of providing healthcare services of any kind, or any kind of services appurtenant to healthcare. This phrase includes any doctor, group practice, any professional other than a physician providing or capable of providing healthcare services, and the like.

The phrase "medical facility", and the like, generally refers to any facility or location, such as a place where medical equipment is located, providing or capable of providing healthcare services of any kind, or any kind of services appurtenant to healthcare. This phrase includes any hospital, department of a hospital, ambulatory care facility, or other location where healthcare services are provided.

In the context of the invention, there is no particular requirement that a medical facility have a fixed location. For example, a medical facility might be an ambulance (with emergency medical care being performed aboard), or might be a "bloodmobile" or similar mobile testing center (with discretionary lab testing being performed for the general public).

The phrase "scoring domain", and the like, generally refers to a category comprised of measures of rankable value applicable to a medical provider, such as affordability and efficiency, patient experience and service, and clinical quality. In a preferred embodiment, scoring domains are generally independent of each other, in the sense that a particular medical provider might achieve a relatively high measure of quality in a $1^{st}$ scoring domain of clinical quality, while achieving only a relatively low measure of cost in a $2^{nd}$ scoring domain of affordability.

For example, a $1^{st}$ medical provider might be ranked 4 stars ("**") for affordability/efficiency, but ranked 2 stars ("") for clinical quality. A $2^{nd}$ medical provider might be ranked 3 stars ("*") for affordability/efficiency, but ranked 4 stars ("**") for clinical quality. In this example, whether a particular user prefers the $1^{st}$ medical provider or the $2^{nd}$ medical provider might depend upon which scoring domain is more important to the user, and how much weight a user decides to place on a medical provider's score (bucket ranking differences).

In a preferred embodiment, the scoring domains include: affordability/efficiency of care, doctor office clinical systems and system modernization, patient experience of service, and clinical quality. However, in the context of the invention, there is no particular requirement that these are the particular scoring domains used. In alternative embodiments, other scoring domains may be used in addition to or in lieu of these particular scoring domains.

The phrase "KPI" (key performance indicator), and the like, generally refers to any data or measurement, in response to which a measure of value can be computed with regard to a medical provider. Each KPI might apply to any one of the scoring domains, such as affordability/efficiency, patient experience and service, and clinical quality. In a preferred embodiment, each scoring domain includes one or more KPI's, from which a composite measure in that scoring domain can be computed. Particular KPI's used with regard to each of the preferred scoring domains are described below.

As described below, preferred embodiments collect data for KPI's from multiple sources. These can include reports already made as part of the healthcare and billing process, such as medical chart information, claims extracts from claims paid directly by patients, prescriptions, and laboratory data. These can also include data from online tools, such as health risk assessments, and other patient survey tools completed by patients as well as completed surveys of doctor office clinical information systems.

The phrase "measure of value", and the like, generally refers to a numeric or otherwise linearly comparable value, applicable to a medical provider in a particular scoring domain. In a preferred embodiment, each scoring domain includes a percentile measure of value, determined in response to one or more KPI's associated with that scoring domain with a defined level of statistical significance.

The phrase "rankable measure", and the like, generally refers to any measure of value in response to which medical providers can be ranked relative to one another.

In a preferred embodiment, each rankable measure includes its response to a bucket ranking, as determined in response to a percentile measure of value with a defined level of statistical significance.

The phrase "intuitive ranking" or "bucket ranking" or "ranking", and the like, generally refers to any measure in which one or more medical providers having similar measures of value in a scoring domain can be grouped. In a preferred embodiment, each distinct bucket ranking would be represented by an associated intuitive presentation (such as 1 star "*" for a bucket ranking of 1, 2 stars "**" for a bucket ranking of 2), and the like. A preferred result might include a presentation from 1 star "*" to 3 stars "*". In a preferred embodiment, bucket rankings presented to a user are statistically valid, (i.e., a user can be confident that a medical provider with a higher bucket rating in a particular scoring domain is objectively better in that scoring domain than a medical provider with a lower bucket rating). For example, in a preferred embodiment, a user has at least a 95% confidence level that a medical provider ranked "*" for quality of medical care is objectively better than a medical provider ranked "" for quality of medical care (e.g., the user can determine that the medical provider with * at the $76^{th}$ percentile is objectively better than a medical provider at ** at the $74^{th}$ percentile).

The phrase "medical condition", and the like, generally refers to any feature of a patient's symptoms, observation, testing or evaluation, diagnosis, medical history, and the like, which are relevant to treatment of that patient.

The phrase "medical treatment", and the like, generally refers to any surgery or other procedure (including prescription of medication, physical therapy, or other activity), and the like, which are relevant to amelioration or prevention of any adverse medical condition for that patient.

The phrase "medical category", and the like, generally refers to a broad or general description of an area of medical practice, such as relating to allergy, heart problems, blood disorders, cancer, and the like.

The phrase "UI" (user interface), and the like, generally refers to any technique, method or system, in which information is presented to users, such as in response to requests made by those users.

The scope and spirit of the invention is not limited to any of these definitions, or to specific examples mentioned therein, but is intended to include the most general concepts embodied by these and other terms.

Further Summary

As described below, the system includes information about medical categories (such as "heart," "allergy," and the like). Within each of these medical categories, the system maintains information about a set of medical conditions (such as "coronary artery disease," "hypertension," and the like), and a set of medical treatments (such as surgeries or other procedures). This has the effect that a user of the system can obtain information regarding medical providers that is specific to their particular medical conditions, medical histories, medical risks, symptoms, and the like.

As described below, the system also includes information about medical providers (including practitioners and facilities). Medical practitioners might include individual doctors, group practices, and other medical personnel such as physical therapists, psychologists, and the like. Medical facilities might include hospitals, specific hospital departments, "urgent care" facilities or other emergency treatment locations, and other medical facilities such as MRI or x-ray examination facilities.

As described below, the system includes a cross-reference of medical conditions with medical treatments (the latter including both surgeries and other procedures). Similarly, the system includes a cross-reference of all medical providers (including both practitioners and facilities) with those medical conditions they have treated, and all medical treatments they have performed. This information is available from reports by those medical providers, such as using requests for reimbursement, patient medical histories, and the like.

In cases where a medical provider has treated a particular medical condition, they are considered capable of performing medical treatments cross-referenced with that medical condition. Similarly, in cases where a medical provider has performed a particular medical treatment, they are considered capable of treating medical conditions that are cross-referenced with that medical treatment. Board-certified specialists in particular areas of medical practice are considered capable of diagnosing medical conditions and performing medical treatments required for their board certification. Similarly, hospital departments accredited in particular areas of medical practice are considered capable of diagnosing medical conditions and performing medical treatments required for their accreditation.

The system also includes a cross-reference of medical practitioners with the medical facilities at which they practice, or to which they refer laboratory work, non-doctor treatment, testing, and the like. This information is available from reports by those medical practitioners, such as using their records of attending on patients at medical facilities, patient medical histories, referring patients to medical facilities, requests for reimbursement, self-reporting of authorization to practice at particular medical facilities, and the like.

Similarly, the system also includes a cross-reference of medical facilities with those medical practitioners they have authorized to practice, or from whom they receive referrals from doctors for hospital admittance, outpatient treatment, laboratory work, non-doctor treatment, testing, and the like. This information is available from reports by those medical facilities, such as using their records of medical practitioners they authorize to attend upon patients, patient medical histories, requests for reimbursement, and the like.

As described below, the system includes, for each medical provider, information about a set of KPI's (key performance indicators), each describing a measure of value in a scoring domain. In a preferred embodiment, some examples of scoring domains include:

Affordability/efficiency—This scoring domain compares each doctor's total cost profile, as well as subcomponent cost profiles, with respect to each specialty, each clinical condition and each surgery or other procedure. Subcomponent costs include those for type and place of service, such as doctor management and surgical costs, hospital, laboratory, x-ray and other medical testing, outpatient hospital (ambulatory facility) costs, and pharmacy. Each doctor's total costs are adjusted for case mix and severity equivalence, negotiated differences in insurer fee schedules, and benefit design, to improve comparability. The term "affordability" is sometimes used herein interchangeably with the term "efficiency." High-level measures relating to affordability include: (1) total patient cost, (2) total patient cost for prescriptions, (3) doctor efficiency relative to a peer group based on a specialty condition index that includes episodes of care (4) doctor efficiency for treatment of that doctor's 10 most common conditions, including episodes of care (5) typical cost per office visit, (6) typical hospital costs, and (7) typical costs for radiology, laboratory, and other medical tests.

Clinical systems—This scoring domain compares each doctor's clinical system, responsive to at least some of the following factors: (1) The doctor's office uses an electronic medical record, (2) The doctor prescribes medications electronically, (3) The doctor uses a patient registry to track patient conditions, (4) The doctor accepts patient e-mail, (5) The doctor provides a personal action plan to help patients, (6) The doctor reviews patient-completed health risk surveys to assess patients' health needs, (7) The doctor provides patient with health education info.

Patient experience/service—This scoring domain compares each doctor's practice with respect to patient experience and service. This includes both factors relevant to the doctor themselves, such as the following: (1) How would the patient rate all their health care at the medical group or clinic? (2) How would the patient rate their personal doctor or nurse? (3) How would the patient rate whether their doctor spends enough time on their medical concerns? (4) How would the patient rate whether their doctor listens carefully to their medical concerns? (5) How would the patient rate whether their doctor explains things clearly? (6) How would the patient rate whether their doctor shows respect for them (and their family when relevant)? This also includes factors relevant to the doctor's staff, such as the following: (1) How would the patient rate their ability to get help or advice by phone? (2) How would the patient rate their ability to get timely care for an illness or injury? (3) How would the patient rate their ability to get a timely appointment for routine care? (4) How would the patient rate their ability to be seen on time when they have an appointment? (5) How would the patient rate staff helpfulness, in general? (6) How would the patient rate staff courtesy and respect, in general?

Clinical quality—This domain uses evidence-based KPI's (Key Performance Indicators) for conditions that may apply to one or more specialties, when comparing a doctor's clinical merit or value within each specialty to a comparable peer group. The phrases "clinical merit" and "clinical value" are sometimes used herein interchangeably with effectiveness. This scoring domain might include several categories of KPIs in response to process, structure, outcomes, access, and experience of care measures. Some broad categories for defining clinical merit or value might include detailed KPI's relating to the following: (1) preventive care for the heart, (2) treatment of congestive heart failure, (3) treatment of coronary artery disease, (4) treatment of hypertension, (5) treatment of multiple conditions including heart disease, (6) post surgery treatment care.

After reading this application, those skilled in the art will recognize that each scoring domain measures a distinct aspect of what the user might be interested in regarding the medical provider. This has the effect that those users who are more interested in affordability can identify those medical providers who are advantageous from that viewpoint, while other users who were more interested in quality of treatment can identify those medical providers who are advantageous from that different viewpoint.

The system determines, for each scoring domain, a composite measure of quality in that scoring domain for each particular medical provider. This is a rankable measure of quality, as users can compare different medical providers with regard to the same scoring domain. Users can compare medical providers based on national, peer group and specialty norms, absolute percentile thresholds or ranges of percentile performance. In preferred embodiments, each distinct bucket ranking would be represented by an associated intuitive presentation (such as 1 star "*" for a bucket ranking of 1, and 2 stars "**" for a bucket ranking of 2), and the like, with the effect that comparisons users make would be relatively easy and intuitive.

The system also assures that these bucket rankings are statistically valid, with the effect that when a user compares different medical providers using bucket rankings, they can be substantially confident (preferably at a 95% confidence level or better) that medical providers with a $1^{st}$ bucket ranking are statistically different from medical providers with a $2^{nd}$ bucket ranking.

The system also provides users with bucket rankings for medical providers when information about their medical provider KPI is restricted in response to patient medical condition, patient medical history, patient symptoms, other restrictive conditions imposed by the user (such as "affordability is most important to me" or such as "being physically convenient to attend appointments is most important to me"), and the like. Notwithstanding the relatively limited data available when users restrict the universe of possible medical providers, the system is capable of providing statistically valid bucket rankings for user comparison. In preferred embodiments, if the universe of possible medical providers is restricted to a very small size, or if there are too few data points, so that bucket rankings whose distinctness is not statistically valid, the system would present some symbol such as "N/A" to indicate that comparative information is not available in meaningful form, due to small sample size.

As described below, the system provides detailed information for medical providers with regard to the KPI's used to determine the bucket rankings. For example, with regard to affordability, the system provides to users its transformed data regarding actual cost or logarithmic cost using standard deviations (to the patient and their insurer) for that medical provider, for that medical condition, for that medical treatment (i.e., surgery or procedure), for patients in that demographic category, with that medical history, with known other conditions, and the like. In the case of affordability, the transformed data might be expressed in dollars; however, in the case of a different scoring domain, the transformed data might be expressed in some other terms, such as a ratio (numerator and denominator comprised of interventions) or index (standard score).

The scope and spirit of the invention is not limited to this further summary, or to specific examples mentioned therein, but is intended to include the most general concepts embodied by this further summary.

System Elements

FIG. 1 shows a block diagram of a system including a doctor performance evaluation tool.

A system 100 includes elements as shown in the figures and the Incorporated Disclosures, including at least a medical provider station 110, a user station 120, a communication link 130, and an evaluation server 140 (the latter including the doctor cost and quality evaluation tool).

The medical insurer station 110 includes an insurer administrator 111 and an insurer workstation 112. In a preferred embodiment, the administrator 111 includes one or more personnel authorized by the insurer to operate the workstation 112. However, in the context of the invention, there is no requirement that the administrator 111 is an actual human being. In alternative embodiments, the administrator 111 might include a computer program interface from the insurer to the system 100, such as a CRM (Customer Relations Management) system or an AI (Artificial Intelligence) program, or other software agent.

The insurer workstation 112 includes elements known for use in computer workstations, including a processor, program and data memory, mass storage, at least one input element capable of receiving insurer input data 113, and at least one output element capable of presenting insurer output data 114. In a preferred embodiment, the input data 113 includes information for input to the evaluation server 140, such as information regarding medical providers and patient interaction with them. Such information might include, e.g., a listing of medical provider specialties, and the like.

The user station 120 includes the capability for a user 121 to operate a user workstation 122. In a preferred embodiment, the user 121 includes an individual, such as a patient, or a representative of an insurer responsible for the patient's healthcare costs. As noted above, in the context of the invention, there is no requirement that the user 121 is an actual human being. In alternative embodiments, the user 121 might include a computer program interface from an insurer to the system 100, such as a CRM system or an AI program, or other software agent.

The user workstation 122 includes elements known for use in computer workstations, including a processor, program and data memory, mass storage, at least one input element capable of receiving user input data 123, and at least one output element capable of presenting user output data 124. In a preferred embodiment, the input data 123 includes requests for information directed to the evaluation server 140, such as information regarding the user's doctor satisfaction survey experience as described above. In a preferred embodiment, the output data 124 includes responses from the evaluation server 140 to those requests, and other data from the evaluation server 140 such as medical provider costs based on user selection criteria and preferences.

The communication link 130 includes elements for receiving data from, and sending data to, the medical provider workstation 112, the user workstation 122, and the evaluation server 140. In a preferred embodiment, the communication link 130 includes connections between the Internet and each of the medical provider workstation 112, the user workstation 122, and the evaluation server 140. However, in the context of the invention there is no requirement for a particular type of communication technique.

The evaluation server 140 includes elements known for use in computer servers, including a processor, program and data memory, mass storage, and software capable of receiving requests, recognizing their content, and sending responses to those requests. The evaluation server 140 includes a UI (user interface) 150 and a doctor performance evaluation tool database 160.

Figures 2, 3, 4, 5, 6, 7, 8, 9, 10, 11, 12, 13, 14, 15, 16:
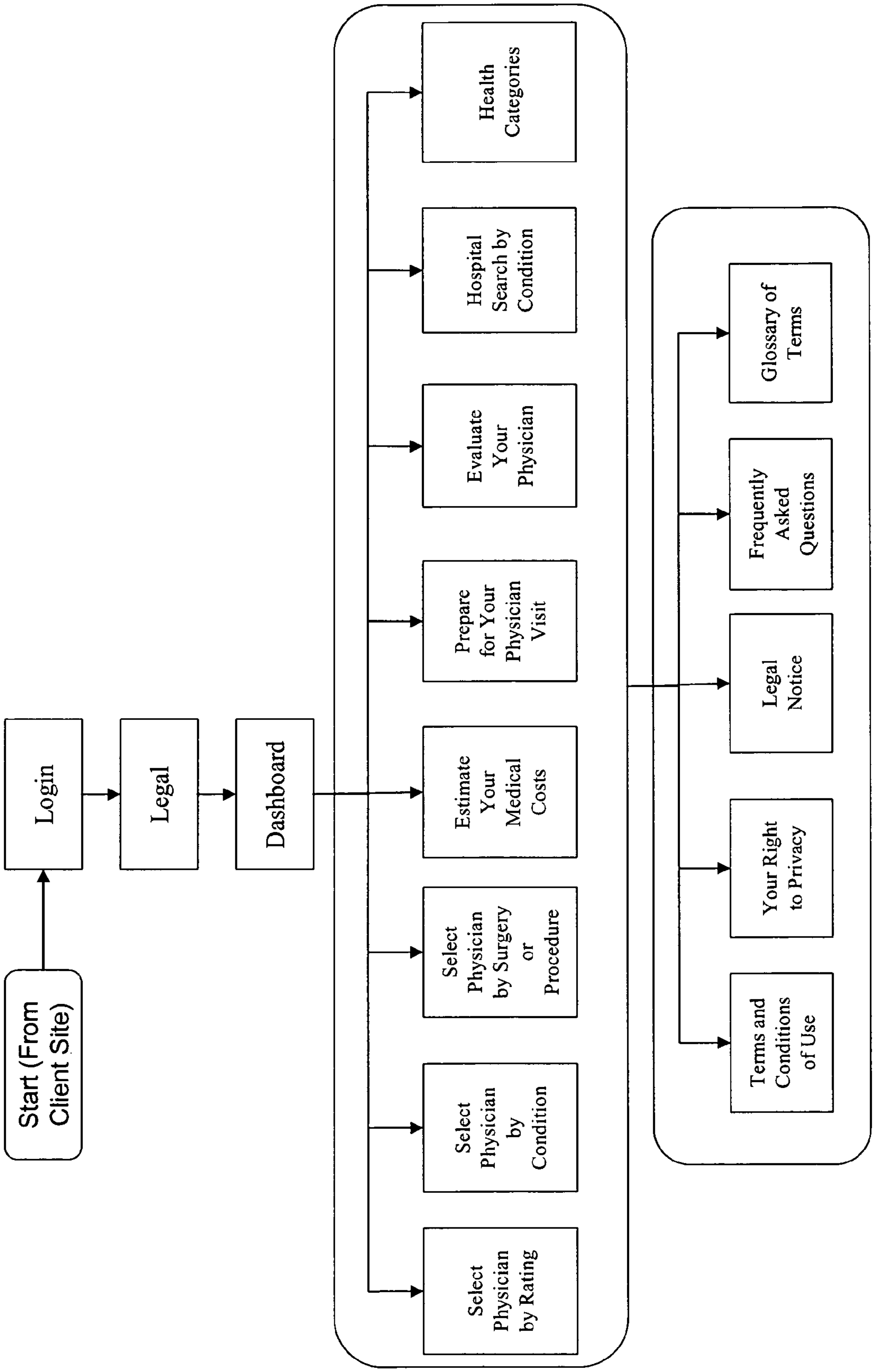
Figures 2, 3, 4, 5, 6, 7, 8, 9, 10, 11, 12, 13, 14, 15, 16, 17:
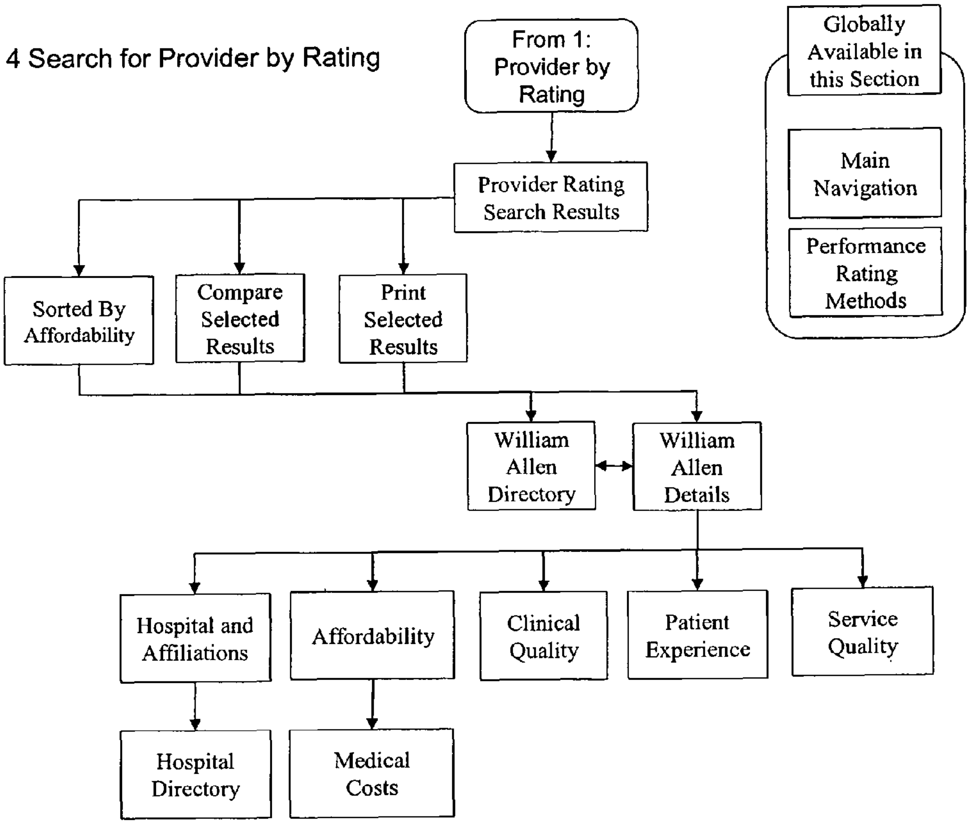
Figures 2, 3, 4, 5, 6, 7, 8, 9, 10, 11, 12, 13, 14, 15, 16, 17, 18:
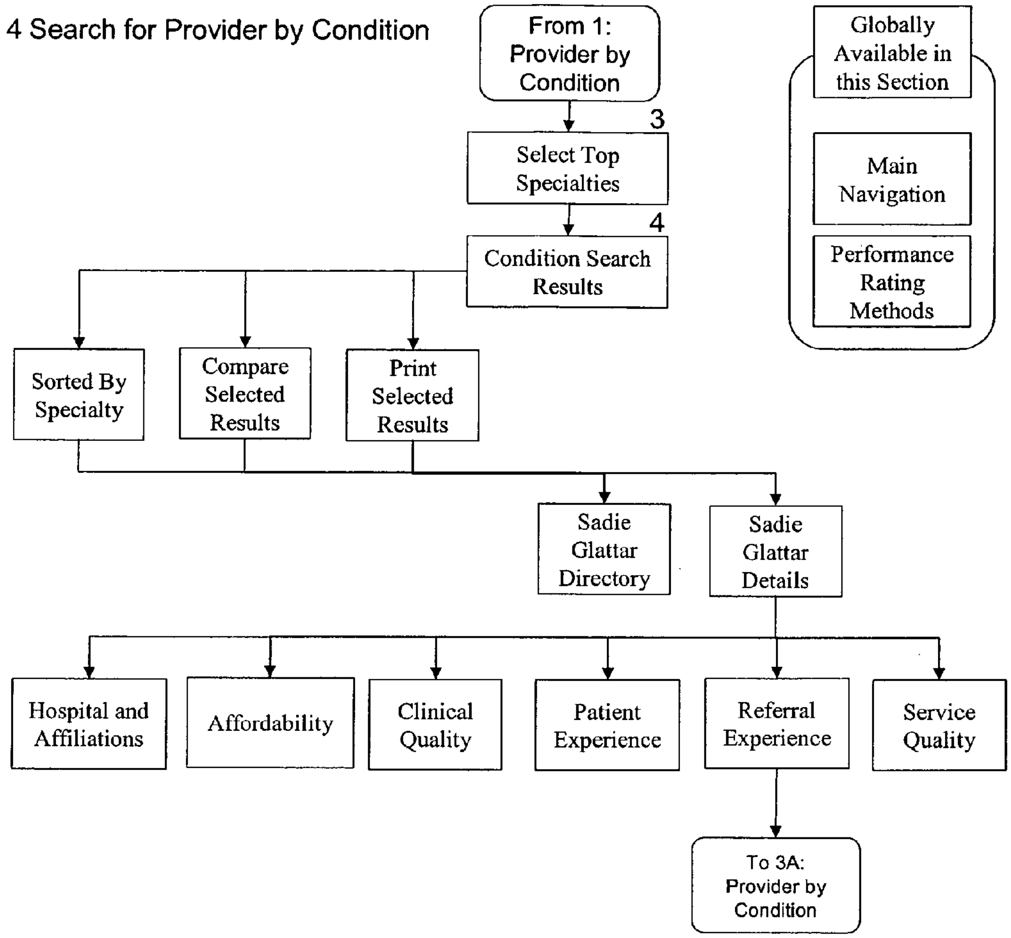
Figures 2, 3, 4, 5, 6, 7, 8, 9, 10, 11, 12, 13, 14, 15, 16, 17, 18, 19:
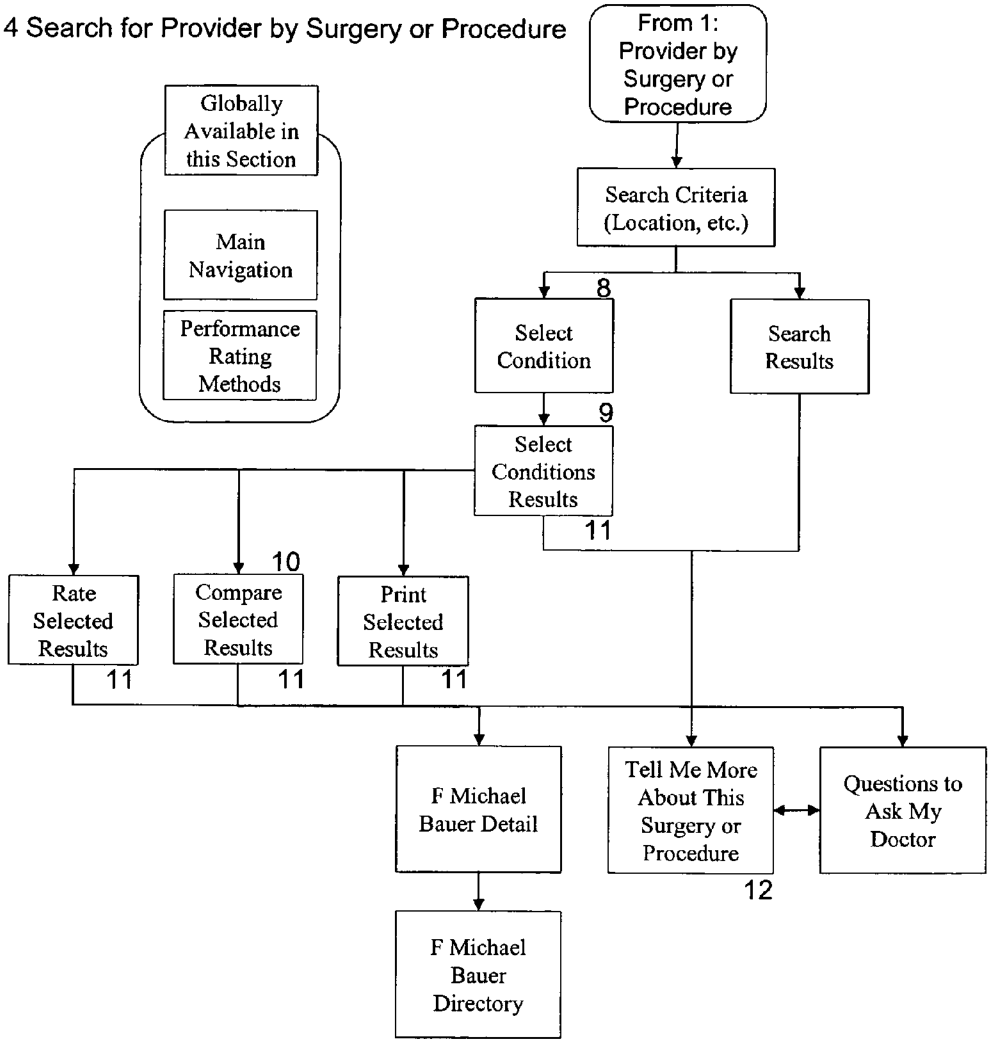
Figures 2, 3, 4, 5, 6, 7, 8, 9, 10, 11, 12, 13, 14, 15, 16, 17, 18, 19, 20:
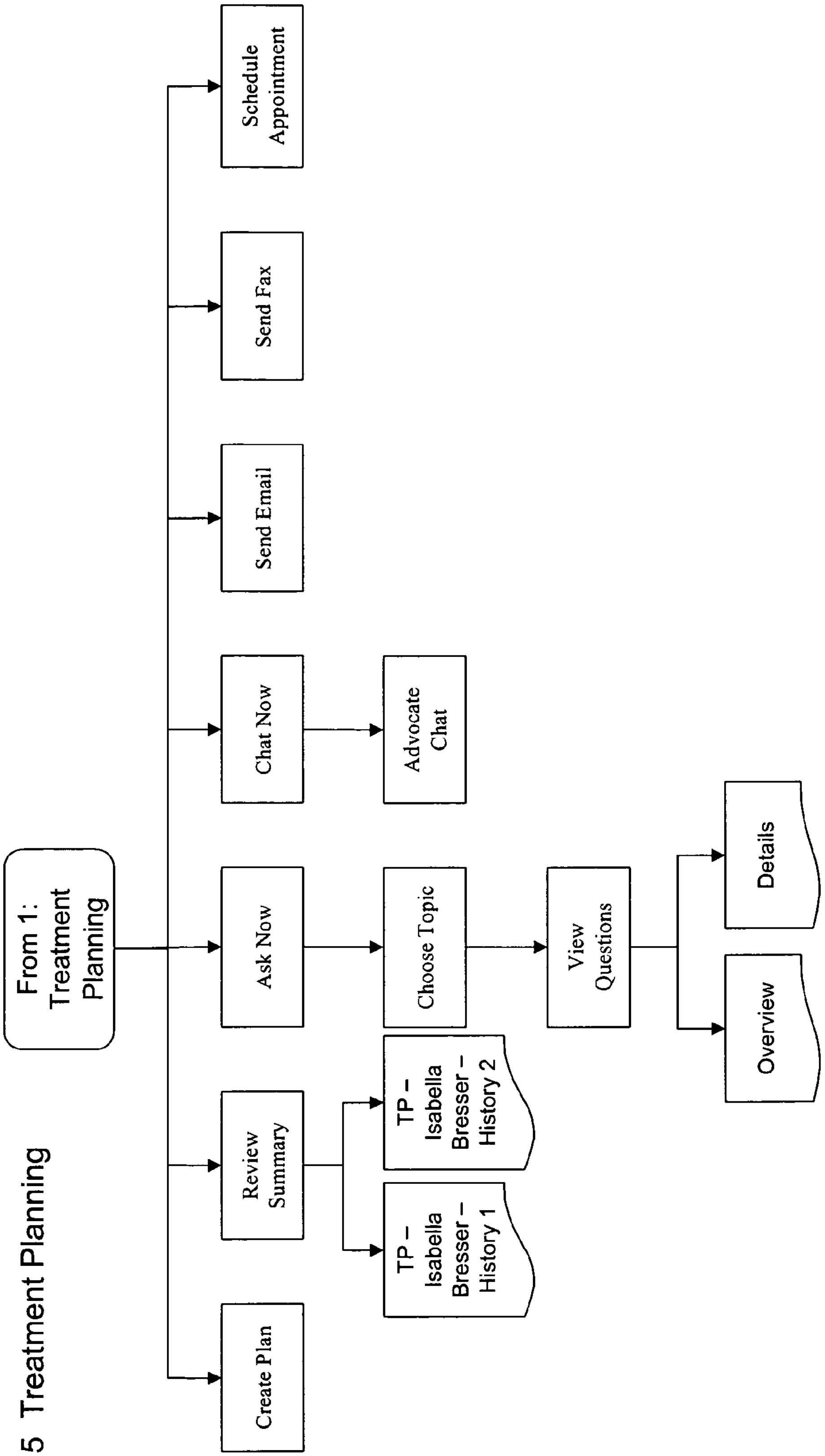
Figures 2, 3, 4, 5, 6, 7, 8, 9, 10, 11, 12, 13, 14, 15, 16, 17, 18, 19, 20, 21:
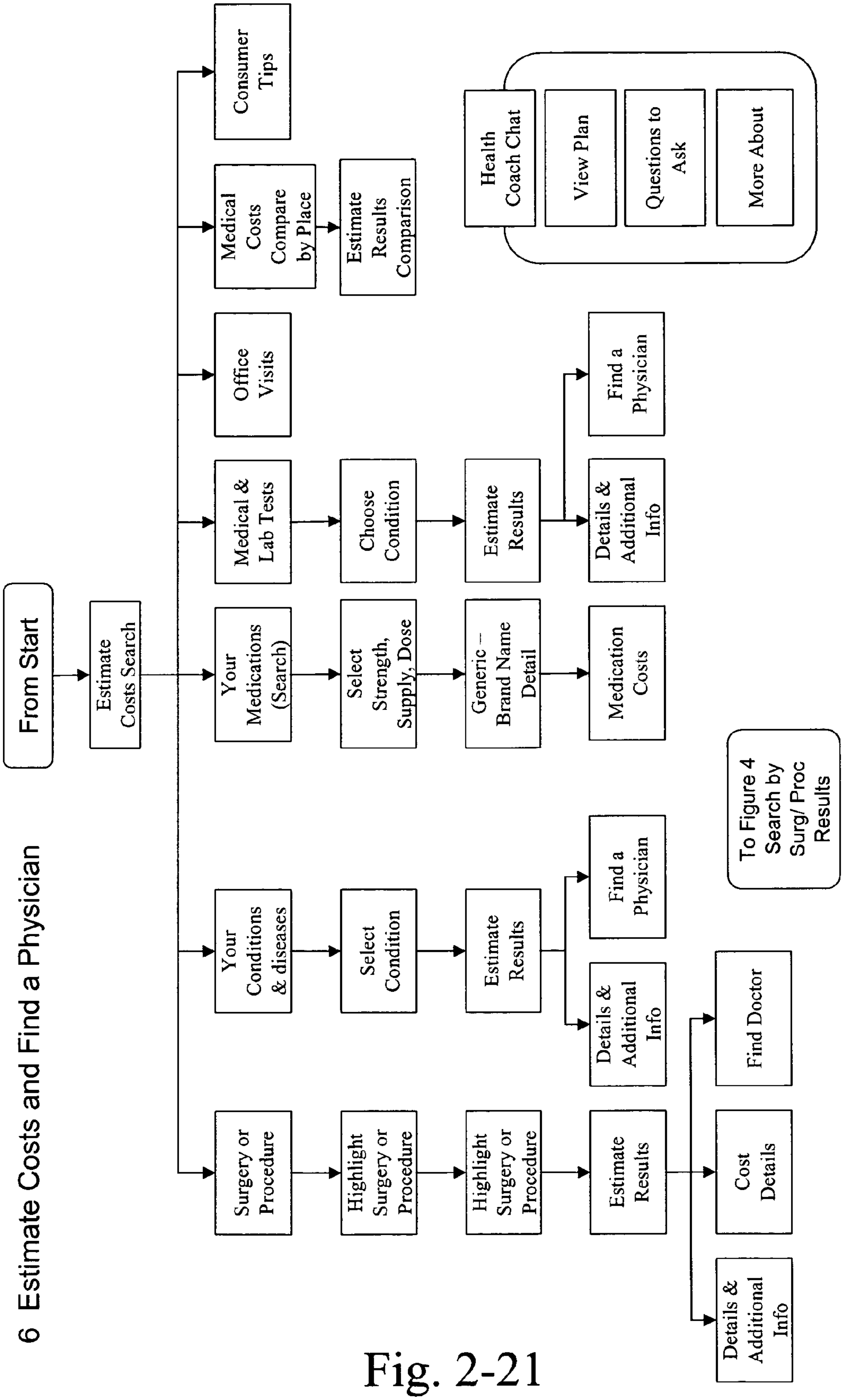
Figure 3:
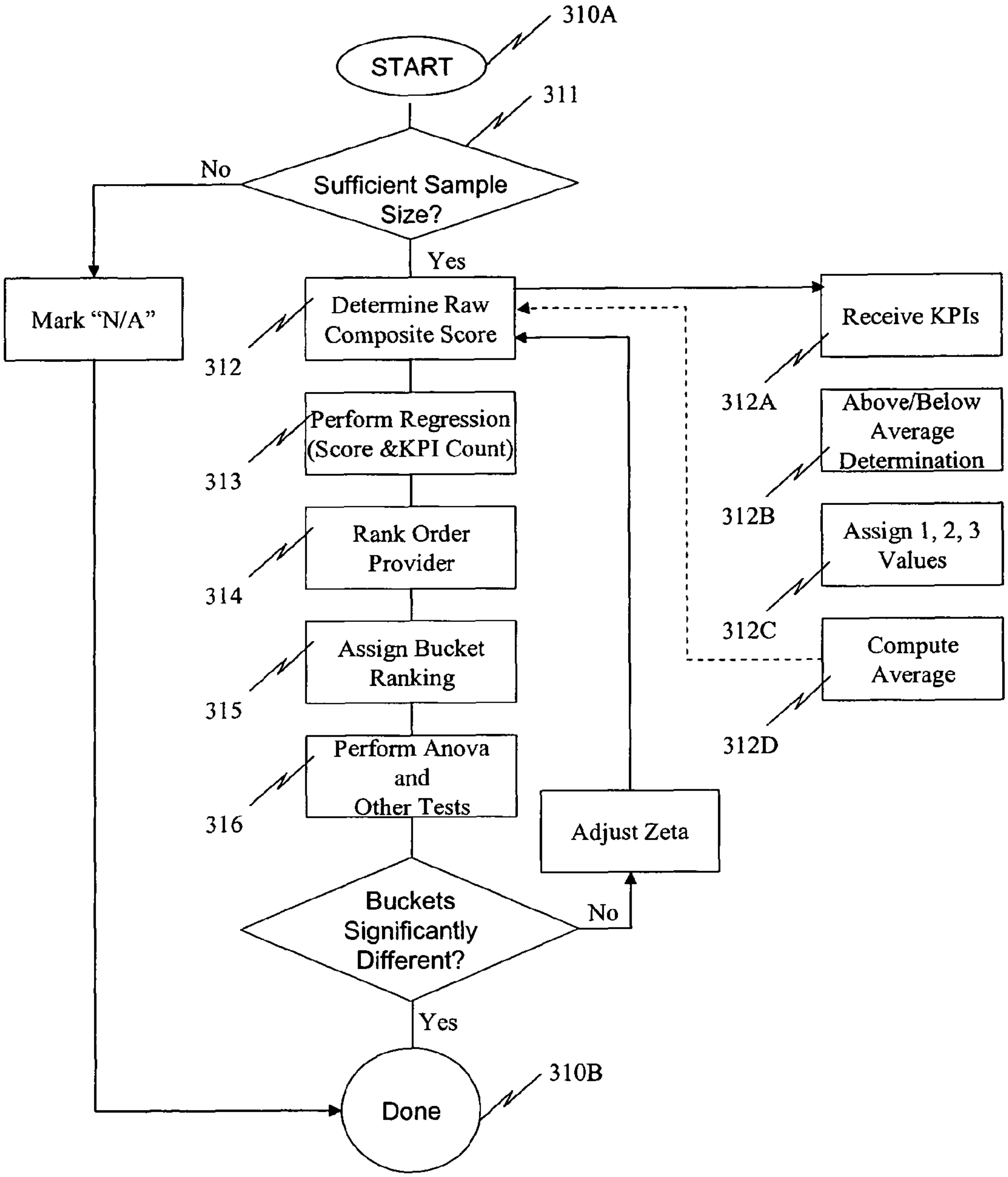

The UI 150 includes a set of screenshots 151 and a set of navigation links 152 as shown in FIG. 2 (including FIG. 2-1 through FIG. 2-21, collectively referred to herein as FIG. 2). The UI 150 receives user input data 123 from the user 121, and presents user output data 124 to the user 121, using one or more of the screenshots 151. As described with regard to FIG. 2, each of the screenshots 151 is suited for presenting or receiving data, or both. The UI 150 presents the navigation links 152 to the user 121, and receives requests from the user 121 to navigate among the screenshots 121 using the navigation links 152. As also described with regard to FIG. 2, each of the navigation links 152 is suited for transfer of context between an originating screenshot 151 and a destination screenshot 151.

The doctor performance evaluation tool database 160 includes a set of information tables and a set of cross-indexing information relating those information tables. The information tables include a medical condition table 161, a medical treatment table 162, a medical practitioner table 163, and a medical facility table 164. As shown in the figure, these tables are pairwise fully cross-indexed, with the effect that it is relatively simple for the database 160 to provide, e.g., those treatments (surgeries or other procedures) associated with each particular condition, and the like.

- Medical conditions are fully cross-indexed with medical treatments, with the effect that the user 121 can readily determine those medical treatments associated with medical conditions they know themselves to have. This information is preselected and supplied by the system 100.
- Medical providers (as maintained in the practitioner table 163 and the facility table 164) are fully cross-indexed with medical conditions, medical surgeries, and medical treatments, with the effect that the user 121 can readily determine which medical providers are capable of treating those medical conditions and performing those medical treatments. This information is determined from records of patient contacts with medical providers.
- Medical practitioners are fully cross-indexed with medical facilities, with the effect that the user 121 can readily determine which medical providers are available at which medical facilities, and with the effect that the evaluation server 140, using the database 160, can compare medical practitioners with practice norms at their particular medical facilities. This information is provided by medical practitioners and medical facilities, and determined from records of patient contacts with medical providers.
- Fully cross-indexing the medical practitioner table 163 with the medical facility table 164 provides an additional capability. When the evaluation server 140 learns that a particular medical practitioner provides healthcare for particular medical conditions and medical treatments, the evaluation server 140 can conclude that medical facilities associated with that particular medical practitioner do so also. Similarly, when the evaluation server 140 learns that a particular medical facility provides healthcare for particular medical conditions and medical treatments, the evaluation server 140 can conclude that medical practitioners (at least those qualified in the same or similar medical group) associated with those medical facilities do so also.

The medical condition table 161 and the medical treatment table 162 are organized into medical categories, with the effect that the user 121 can browse the various medical conditions and medical treatments with only coarse knowledge of healthcare. In alternate embodiments, the medical condition table 161 and the medical treatment table 162 may also be organized in response to other factors, such as cost, frequency of occurrence, risk, and the like.

The medical practitioner table 163 and the medical facility table 164 are organized into physical regions and into medical specialties, with the effect that the user 121 can browse those medical providers available in their local area, and with effect that the user 121 can browse those medical providers with regard to those medical specialties the user 121 considers most important.

The doctor performance evaluation tool database 160 also includes a diagnoses table 165, and an episode of care table 166. The diagnoses table 165 and the episode of care table 166 are fully cross-indexed. The diagnoses table numeral 165 is indexed with the medical condition table 161 and the medical treatment table 162, with the effect that the database 160 maintains a record of diagnoses made by particular medical providers with regard to selectable medical conditions and medical treatments. Similarly, the episode of care table 166 is also indexed with the medical condition table 161 and the medical treatment table 162, with the effect that the database 160 maintains a record of diagnoses made by particular medical providers with regard to selectable medical conditions and medical treatments. As described below, the evaluation server 140 can use these data in determining measures of quality for medical providers in one or more scoring domains.

In preferred embodiments, individual diagnoses maintained in the diagnoses table 165 might correspond to standardized codes for diagnosis, such as ICD-9CM codes or ICD-10CM codes, and the like. Similarly, individual medical treatments in the medical treatment table 162 might correspond to standardized codes for surgeries and other procedures, such as CPT codes or HCPC codes, and the like.

In preferred embodiments, individual medical conditions in the medical conditions table 161 might correspond to a collection of possible diagnoses (and these collections might overlap, with the effect that a particular diagnosis can be associated with more than one medical condition). Similarly, individual episodes of care in the episode of care table 166 might correspond to a collection of possible medical treatments (and these collections might overlap, with the effect that a particular episode of care can be associated with more than one medical treatment).

In preferred embodiments, individual medical diagnoses and individual medical treatments might each be associated with a date at which the medical provider made that diagnosis or the medical provider performed that treatment. Individual medical conditions and individual episodes of care might each be associated with a sequence of dates, or a time duration, during which the medical provider deemed that medical condition to be extant, or during which the medical provider deemed the type of care to be ongoing.

The doctor performance evaluation tool database 160 maintains those measures of quality for each medical provider in one or more scoring domains, in response to KPI's (key performance indicators) associated with the medical conditions and mental treatments in the healthcare practice areas for those medical providers. This has the effect that the user 121 can browse the set of medical providers and obtain statistically valid intuitive bucket rankings (such as 1 star "*" to 3 stars "*"). The user 121** can also restrict the set of medical providers when browsing to particular medical conditions, medical treatments, physical regions, and the like, while still obtaining statistically valid intuitive bucket rankings.

User Interface

FIG. 2 (including FIG. 2-1 through FIG. 2-22, collectively referred to herein as FIG. 2) shows a set of screen shots (FIG. 2-1 through FIG. 2-15) and navigation flowcharts (FIG. 2-16 through 2-21) for a doctor performance evaluation tool.

FIG. 2-1 is a screen shot for the invention illustrating how users 121 can select medical providers by rating based on specialty, benefit plan, language spoken, gender of the medical provider (doctor), and zip code driving distance from user location (work or home address).

Generally, the user 121 selects the criteria for the search from a list of possible choices for each category. For example, the "language" category could include all the languages spoken by providers stored in the system.

FIG. 2-2 is a screen shot that shows how users 121 can select medical providers based on their condition, symptom or diagnosis; by selecting the conditions "congestive heart failure and hypertension," the user 121 can then select "View Condition Information" to identify which fields (specialties) treat these conditions.

Generally, the user 121 makes their selection from lists of available choices using drop-down lists, radio buttons and the like. This eliminates the possibility of spelling errors. Many different selection criteria are available for user 121 convenience as is evidenced in the screen shot.

FIG. 2-3 is a screen shot that shows how users 121 can identify which specific specialties they would like to review for purposes of treating their congestive heart failure and hypertension conditions.

FIG. 2-4 is a screen shot that has a spreadsheet format with columns and rows that shows that once a user 121 selects the one or more fields (specialties), the user 121 can then review all medical providers who treat the user's condition or diagnosis for congestive heart failure and hypertension based on the user's location and benefit plan coverage; after viewing all the medical providers, the user 121 may then drill down into the individual medical provider's detailed ratings for further rating review purposes.

This screen shot illustrates a list of physicians that treat the condition of Congestive Heart Failure (CHF). This screen is displayed in response to the user 121 selecting the condition of CHF.

FIG. 2-5 is a screen shot that illustrates how the invention can provide detailed rating information for each medical provider; users may look up further information of the measures that are comprised in each scoring domain, such as clinical quality.

This screen shot shows rating information for Doctor William Allen in Cardiology. Several rating factors are listed along with the bucket rating of 1, 2, 3 or 4 stars.

FIG. 2-6 is a screen shot that illustrates how the invention can provide additional drill down information on each category for each individual medical provider; in this example, the user 121 has drilled down into the individual clinical quality measures that are relevant to this individual medical provider and specialty; the invention uses a method to generate measures that are specific to each individual medical provider and specialty; in addition, the invention uses a statistical methodology to ensure that each measure or KPI has sufficient patient sample size based on a level of confidence to be reported to users 121. For example, if the individual measure in the third row has an insufficient patient population sample size or data, the measure is reported as "N/A (not available)" for the individual medical provider. This statistical sampling algorithm reviews for sufficient sample size to assure a stable result. This invention also illustrates the method used to report patient compliance rates for measure by individual provider as well as comparisons with national average norms, in the last column, with other similar medical providers using a percentile calculation methodology.

In a preferred embodiment, a percentile ranking is used as the score for each KPI. Thus, the overall score for an individual medical provider is the average of all the percentile rankings for each KPI in a domain, such as clinical quality. The invention provides an overall score for measures in each scoring domain. The overall score under "Doctor Rating" represents a composite score for several KPIs. The composite score is an average of the individual medical provider's bucket ranking scores (i.e., star ratings) statistically adjusted for the number of KPIs per individual medical provider. The overall composite score controls for the number of individual KPIs in each domain. For example, if there are 15 KPIs in the clinical quality domain, and some medical providers have 5

KPIs and others have 9, 11, and 15 respectively, the composite score controls for the differences in number of KPIs which affect the average score of the individual medical provider. The doctors are then re-ranked and placed in buckets based on their percentile standing on this new aggregate/composite scale.

This screen shot illustrates how the invention can provide additional drill down information on each category for each individual medical provider. In this example, the user has drilled down into the individual clinical quality measures that are relevant to this individual medical provider and specialty. The invention uses a method to generate measures that are specific to each individual medical provider and specialty. In addition the invention uses a statistical methodology to ensure that each measure or KPI has sufficient patient sample size based on a level of confidence to be reported to users. For example, in this figure, if the individual measure "treatment of patients with CAD" did not have a sufficient enough sample size to be statistically meaningful, the physician rating column would contain "N/A" instead of a star bucket ranking. This invention also illustrates the method used to report patient compliance rates for measures by individual provider as well as comparisons with national average benchmarks, and finally in the last column, with other similar doctors using a percentile calculation methodology.

FIG. 2-7 is a screen shot that illustrates how the invention can link individual medical providers with their hospital affiliation so that users 121 can identify what percent of doctor's total patient population are admitted by hospital; in addition, this invention also illustrates how users 121 can identify clinical quality, service quality, patient experience, and affordability of hospitals used by this individual medical provider; finally, this screen shot illustrates how this invention shows the medical provider's affiliation with a group practice, if relevant.

This screen shot illustrates how the invention can link individual medical providers with their hospital affiliations so that users can identify what percent of a doctor's total patient population are admitted by hospital. In addition, this invention also illustrates how users can identify clinical quality, service quality, patient experience, and affordability of hospitals used by this individual medical provider. This screen also illustrates how this invention shows the doctor's affiliation with a group practice, if relevant.

information for a Doctor William Allen who practices Cardiology. This exemplary screen shot illustrates the hospital affiliation information displayed in a row and column format.

FIG. 2-8 is a screen shot that illustrates how users 121 can select i) their specific health issue (Heart), then ii) select the surgery or procedure (coronary artery bypass surgery—open heart surgery) relevant to their specific health issue, iii) view a brief description of the surgery; after highlighting the surgery or procedure, the user 121 can then locate individual medical providers that treat for the specific surgery or procedure; alternatively, the invention has created a taxonomy database whereby the user 121 can type in a procedure in the box titled "Search for Your Surgery or Procedure" to review individual medical providers that perform the surgery or procedure.

Generally, the user 121 makes a selection from a list as illustrated in the screen shot. By selecting a health issue and procedure in this way, the user can find a physician that is associated with treating this type of condition.

FIG. 2-9 is a screen shot that shows that once users 121 select a surgery or procedure, they can then see the individual medical providers who perform this service, the number of patients who had this service by individual medical provider and the total cost for the service and the user's total out of pocket cost based on the user's benefit plan design (e.g., deductible or co-insurance liability).

As with most screens, several data items displayed are underlined indicating that drilling down to a more detailed level is possible for that data item.

FIG. 2-10 is a screen shot that shows users 121 may also compare one or more individual medical providers with each other by checking the "Select" box for each medical provider.

This feature allows the user 121 to more closely scrutinize the providers they are most interested in. In the screen shot only three providers are listed, but it is quite possible that 20 or more providers could be listed.

FIG. 2-11 is a screen shot that shows users 121 can also find more health education information or identify the questions they need to ask their doctor regarding their specific condition, surgery or treatment; the invention customizes the health education content based on the user's selected treatment.

Users 121 can also find out more health education information or identify the questions they need to ask their doctor regarding their specific condition, surgery or treatment. The invention customizes the health education content based on the user's selected treatment. Generally, a more informed patient is better for the physician as well as the patient.

FIG. 2-12 is a screen shot that illustrates how the invention allows users 121 to select health education content that is highly personalized and relevant to the user's specific treatment needs.

The user 121 has selected a path that allows the system to present to the user 121 choices for additional data and education that are pertinent and essentially customized to the user's needs.

FIG. 2-13 is a screen shot that illustrates how the invention enables users 121 to prepare for their doctor office visit by selecting among a number of preparation tools; these preparation tools, in descending order, include the ability of the user 121 to 1) complete a health risk assessment survey to understand their personal risk factors and what actions to take (e.g., change diet, quit smoking, etc.), 2) review the electronic patient health record, 3) ask questions of their doctor based on their specific condition, 4) e-mail or perform Internet chat functions with a nurse advice service, 5) send an e-mail to their doctor, 6) fax important medical information or questions to their doctor, and 7) schedule an online appointment with their doctor.

It is a core duty of a good physician to set a patient's mind at ease. Medicine has its own terminology and procedure that is rarely understood by those not in the business of health care. This screen shot illustrates some of the resources available to the user 121, so they can prepare for their visit and even start a dialog with the physician via email prior to the visit.

FIG. 2-14 is a screen shot that illustrates how the invention enables the user to estimate medical costs for a given condition and subsequently find a physician that specifically serves that condition.

Generally, the user 121 selects their health issue and condition from a list and also selects the level of the condition. A description of the condition can assist the user 121 in selecting the correct severity level.

FIG. 2-15 is a screen shot that illustrates how a user can find a physician serving a specific condition after having reviewed the average medical costs for that condition.

This screen shot illustrates how the system breaks down the cost into categories (Physician, Lab, and Hospital), and it shows what portion the user 121 can expect the insurance to cover and what they may be responsible for.

FIG. 2-16 is a flow chart that illustrates high level navigation for user selection of menu options.

This flow chart illustrates the navigation and functions performed by a computer program product. The flow chart illustrates how a user 121 can navigate to select one or more service providers based on a plurality of indicia.

FIG. 2-17 is a flow chart that illustrates user selection of a service provider based on criteria (indicia) for benefit plan type, location, gender, accepting new patients, specialty, and individual service provider last name. The invention uses computer readable code to query a database of individual service providers by specialty and group practice. The invention uses a method of associating the plurality of indicia to each service provider (e.g., affordability, clinical quality, etc. to William Allen, MD.) which are stored in a database. The invention extracts health care information data and uses methods to transform this data into indicia and percentile rankings by individual service provider. The invention also groups indicia into a plurality of categories and to create an overall percentile ranking for the service provider. The user may then select and compare the ratings of one or more service providers and drill down into the ratings of each individual service provider.

FIG. 2-18 is a flow chart that illustrates that the user 121 can select a service provider based on their condition, diagnosis or symptom and indicia such as benefit plan type, location, gender, and languages spoken by the service provider. The invention uses a method for associating the medical condition, diagnosis, or symptom of a user to each service provider in the database. The invention uses computer readable code to query a database of individual service providers that treat certain conditions, diagnoses or symptoms of patients. The invention extracts health care information data and then uses methods to transform this data into indicia and percentile rankings by individual service provider based on the user's condition, diagnosis or symptom. The user may then select and compare the ratings of one or more service providers and drill down into the ratings of each individual service provider. A user can also search the database for the specialist referral experiences of individual primary care service providers. The user can review the quality, cost and patient service experiences of referrals made by these primary care providers.

FIG. 2-19 is a flow chart that illustrates that the user can select a service provider based on the user's need for a surgery, medical procedure, and other indicia (benefit plan type, location, gender, languages spoken). The invention has a method of associating the surgery or procedure to each service provider in the database. The invention uses computer readable code to query a database of individual service providers that perform the specific medical procedure or surgery requested by the user. The invention extracts health care information data and then uses methods to transform this data into indicia and percentile rankings by individual service provider based on the user's requested surgery or medical procedure. The user may then select and compare the ratings of one or more service providers and drill down into the ratings of each individual service provider that perform the surgery or procedure. The invention also uses methods to extract and calculate the cost of the surgery or medical procedure for the insurance company and for the user.

FIG. 2-20 is a flow chart that illustrates the organization of treatment planning information for the user 121 before the user 121 sees a service provider. The user 121 can plan their treatment before visiting their selected service provider by 1.) reviewing and printing a brief summary of the electronic patient health record of the user 121, 2.) generating questions to ask their doctor for the specific condition or treatment they will require, and 3.) faxing relevant information to the office of the physician in advance of their visit.

FIG. 2-21 is a flow chart that illustrates the organization of medical and lab cost information for the user 121. The user 121 may search for medical and lab costs for a given condition, surgery or procedure and subsequently locate a physician providing a service for that condition, surgery or procedure.

Method of Operation

FIG. 3 shows a process flow diagram of a method including determining a composite score for measures of quality for medical providers.

As described below, this novel method allows the system to provide intuitive, meaningful, and statistically valid composite scores for a greater number of medical providers than known methods.

As described herein, when using an average (even a weighted average) of KPI's, it is extremely difficult to meaningfully assign doctors with distinct bucket rankings, because those bucket rankings are, in general, not statistically valid. Users 121 cannot tell with a reasonable degree of confidence (in a preferred embodiment, at a 95% confidence level, but other degrees of confidence might be used) that a $1^{st}$ medical provider with a bucket ranking of 3 stars ("*") is truly better than a $2^{nd}$ medical provider with a bucket ranking of 2 stars (""). There is still a substantial probability that random factors may have operated to cause the $1^{st}$ medical provider to score better than the $2^{nd}$ medical provider, without merit dictating that result.

As described herein, when users 121 have a greater number of medical providers whom they can meaningfully evaluate, those users 121 have increased choice. For example, more doctors and more group practices would be displayed in a provider directory with bucket rankings, whereas in known systems those doctors and more group practices would appear without bucket rankings, or would not appear at all. When users 121 have increased choice, patient satisfaction is improved, medical care can be improved, and cost-effectiveness can be improved.

Moreover, as described herein, this novel method allows the system to provide intuitive, meaningful, and statistically valid composite scores, even when the user 121 has significantly restricted their search domain of medical providers. That significant restriction might be in response to the user's particular medical conditions, medical history, and the like, as described above. That significant restriction might also be in response to "more mundane," but often just as important to consumers, conditions, such as an individual doctor's gender, the distance from the consumer's home or work, or whether the medical provider accepts the consumer's benefit plan and insurance coverage.

A method 300 includes a set of flow points and steps. Although described serially, these flow points and steps of the method 300 can be performed by separate elements in conjunction or in parallel, whether asynchronously or synchronously, in a pipelined manner, or otherwise. There is no particular requirement that the flow points or steps are performed in the same order as described, except where explicitly so indicated. Those skilled in the art will understand that the number and types of entities that can exist in the supply chain and that are used in the figures are illustrative and not intended to be limiting.

The method 300 includes flow points and process steps as shown in the figure, plus possibly other flow points and process steps as described in the incorporated disclosure. These flow points and process steps include at least the following:

A pair of flow points 310A and 310B, a set of steps performed in between, and a flow point 310C in between, in which the method 300 determines a composite score for measures of quality for medical providers.

At a flow point 310A, the method 300 is ready to determine a composite score for measures of quality, cost, or other criteria for medical providers.

At a step 311, the method 300 determines if the sample size of data for the particular medical provider for each KPI, in a particular scoring domain, is large enough to assure a 95% confidence level for computation of the bucket ranking (as described below). If the sample size is not large enough (in preferred embodiments, fewer than 4 KPI's), the method 300 skips the process of determining a composite score, and proceeds to the flow point 300B. As described above, the system 100 considers the bucket ranking for that medical provider in that scoring domain to be unavailable. If a user 121 asks for a display of the composite score for a medical provider for which the system will not compute one, the system displays a symbol indicating that no such composite score is available, such as the marker "N/A", for "not available" or "not applicable." Although a 95% confidence level is used in this step, in the context of the invention, there is no particular requirement for this specific confidence level, and in alternative embodiments, the method 300 might use a 90% confidence level, a 98% confidence level, or some other useful confidence level based on alpha and beta (power) levels determined by the user 121.

At a step 312, the method 300 determines a raw composite score, as a measure of value for the particular medical provider in the particular scoring domain. In a preferred embodiment, this step includes the following sub-steps:

At a sub step (a), the method 300 receives a set of individual KPI's applicable to the particular medical provider in the particular scoring domain.

At a sub step (b), the method 300 determines, for each individual KPI, whether the particular medical provider is above average, average, or below average with respect to a set of comparable medical providers or above average, average or below average with respect to an absolute threshold value or above average, average or below average against minimum and maximum threshold values.

In this sub step, whether the particular medical provider is "above average" is determined as follows.

(i) determining a confidence range, within which there is a $\zeta_o$=90% degree of confidence that the medical provider's "true" measure of value for that scoring domain should fall;

(ii) determining a similar confidence range for a set of comparable medical providers; and (iii) determining that the range for the individual medical provider is greater than, and does not overlap, the range for the set of comparable medical providers.

Whether the particular medical provider is "below average" is determined similarly, except that to be "below average," the range for the individual medical provider is less than, and does not overlap, the range for the set of comparable medical providers.

If the particular medical provider is neither "above average" nor "below average," the range for the individual medical provider overlaps the range for the set of comparable medical providers, and the particular medical provider is determined to be "average."

After reading this application, those skilled in the art will recognize that the confidence range for the set of comparable medical providers need only be computed once for each time a condign set of comparable medical providers is selected.

After reading this application, those skilled in the art will recognize that the confidence level used in this sub step need not be a $\zeta_o$=95% confidence level. As described below, the confidence level $\zeta_o$ used in this step might be adjusted in other steps of the method 300.

When the confidence level $\zeta_o$ is smaller (closer to 0% and farther from 100%), the confidence ranges determined in response to that confidence level $\zeta_o$ are wider, with the result that more medical providers' confidence ranges overlap the confidence range for the set of comparable medical providers, and fewer medical providers can be assigned meaningful bucket rankings. In contrast, when the confidence level $\zeta_o$ is greater (closer to 100% and farther from 0%), the confidence ranges determined in response to that confidence level $\zeta_o$ are narrower, with the result that fewer medical providers' confidence ranges overlap the confidence range for the set of comparable medical providers, and more medical providers can be assigned meaningful bucket rankings.

In preferred embodiments, the set of comparable medical providers includes all medical providers in the same group practice or hospital department. As part of this sub step, the method 300 makes the same determination, but restricted to a subset of those medical providers, such as only those medical providers who are board-certified in the same medical specialty.

After reading this application, those skilled in the art will recognize that the method 300 has advantages over the "average point" method. The "average point" method has the drawback that substantially all medical providers have confidence ranges which overlap when the confidence level for those ranges is set at a meaningful value (say, a 95% degree of confidence). This has the effect that a chart of medical providers ordered from best to worst looks much like a harmonica—almost no distinctions between medical providers are statistically valid.

As described below, this novel method 300 is able to assign medical providers to bucket values, and to assure that those bucket values are substantially disjoint. This has the effect that the user 121 can be confident that if a $1^{st}$ medical provider has a better assigned bucket value than a $2^{nd}$ medical provider, that $1^{st}$ medical provider really is better than that $2^{nd}$ medical provider (at least for that scoring domain).

At a sub step (c), the method 300 assigns a $1^{st}$ value (preferably 3) for above average medical providers, a $2^{nd}$ value (preferably 2) for average medical providers, and a $3^{rd}$ value (preferably 1) for below average medical providers. In this context, "above average," "average," and "below average" have similar meanings as in the previous sub step. Similar to the previous sub step, the method 300 makes this assignment both in comparison to all medical providers, and in comparison to a subset thereof.

At a sub step (d), the method 300 computes an unweighted average of the values assigned for each KPI in the previous sub step, with the effect of generating a raw score. These unweighted averages are suspect, since they are influenced by the number of KPI's a particular medical provider contributed to the composite. Similar to the previous sub step, the method makes this computation both in comparison to all medical providers, and in comparison to a subset thereof.

At a step 313, the method 300 performs an ordinary least squares linear regression on the function $y_n$=f($x_n$), where $y_n$ is the composite raw score for the $n^{th}$ medical provider, and where $x_n$ is the number of KPI's for that $n^{th}$ medical provider. This has the effect of determining parameters $\beta_o$ and $\beta_1$ for the linear regression function. The linear regression function is $y_n=\beta_o+\beta_1 x_n+E_n$, where $E_n$ is the residual value not accounted for by the number of KPI's for the nth medical provider.

At a step 314, the method 300 rank orders the medical providers by their residual values $E_n$, with high values for $E_n$ being ranked better than low values for $E_n$.

At a step 315, the method 300 assigns a bucket ranking to each medical provider, in response to that medical provider's position in the rank ordering. In a preferred embodiment, the bucket rankings are substantially equal in size, with the effect that if 3 buckets are used, 33% of the medical providers will be assigned to each bucket, while if 4 buckets are used, 25% of the medical providers will be assigned to each bucket. In a preferred embodiment where the bucket rankings range from 1 star "*" to 3 stars "*", the method 300** uses 3 buckets.

At a step 316, the method 300 tests that the set of medical providers assigned to each bucket ranking are statistically different at the $p<0.05$ level for statistical significance. In a preferred embodiment, the method 300 computes a 1-way ANOVA test, with the effect of determining if the residual values $E_n$ can be represented as a relatively simple function $E_n=g(s_n)$, where $s_n$ is the bucket ranking (e.g., the number of stars) assigned to the $n^{th}$ medical practitioner. The method 300 determines if the bucket rankings are statistically different in response to a result of the 1-way ANOVA test.

If the method 300 determines that the bucket rankings are statistically different, those bucket rankings are maintained for display to the user 121 and for use when later asked for. If the method 300 determines that the bucket rankings are not statistically different, the confidence level $\zeta_o$ used in the sub step 312(*b*) is adjusted, and the method proceeds with the beginning of the step 312.

After reading this application, those skilled in the art will recognize that the ANOVA test performed in the step 316 assures that medical providers are allocated to discrete bucket rankings with substantial accuracy. This accuracy is deemed sufficient for users 121 to make decisions in response to those bucket rankings. Similarly, after reading this application, those skilled in the art will recognize that the step 312 provides for display of as many medical providers as possible (such as in a provider directory), consistent with the requirement imposed by accuracy. This has the effect that the method 300 assigns medical providers a set of bucket rankings that provide as much display capability and as much accuracy as simultaneously possible.

At a flow point 310B, the method 300 has determined a composite score for measures of quality for medical providers.

Additional Capabilities

After reading this application, those skilled in the art would recognize that it provides additional capabilities beyond those immediately described herein. Some of these additional capabilities include:

- Ability to search provider with performance ratings by condition, surgery or procedure.
- Ability to compare a doctor's performance on affordability (cost or efficiency), clinical quality, patient experience, clinical systems, and other domains with other doctors who are in the same specialty or to a peer group.
- Ability to compare a doctor's performance on individual KPIs in each domain with other doctors who are in the same specialty or to a peer group
- Ability to look up quality or cost measures that are mapped to patient conditions that are mapped to doctor quality rating scores.
- Ability to look up questions to ask your doctor based on the conditions treated or services performed specifically by that doctor.
- Ability to search a provider by multiple performance criteria such as cost, quality, use of electronic medical record, patient satisfaction survey.
- Ability to establish different performance ratings for doctors on quality measures based on sample size, confidence intervals, relative ranking to a peer group performance against a user 121 defined absolute threshold, performance within an acceptable tolerable range.
- Ability to generate a composite score for a provider across multiple, clinical quality KPIs (measures) where providers have different sample sizes by clinical or cost measure and different numbers of KPIs in which they participate.
- Ability to incorporate multiple domains with measures in each domain defined by the user 121 using a balanced scorecard framework for doctors.
- Ability to compare the costs of surgeries, procedures and treatment of conditions by individual providers, by type of provider (hospital, doctor, ancillary, pharmacy).
- Ability for a patient to compare of cost the treating a condition or having a surgery or procedure by different delivery settings in the patient's community by individual provider (hospital, ambulatory surgery center, outpatient hospital, doctor office).
- The ability to look up treatment guidelines, questions to ask your doctor, and explanations of a condition, treatment or procedure that is related to the patient's search for a doctor that can treat the patient for a specific ailment.
- The ability to establish multiple thresholds (loose too strict) for assigning patients to doctors without forced HMO gatekeeper assignment for purposes of tracking which doctors have been responsible for a patient's care for a specific quality measure. This reduces the false positive rate for identifying which doctors are truly managing the patient's care.
- The ability to create a patient registry of patients by quality measure for an individual doctor to follow up. The lists identify patients assigned to a responsible provider and identify individual patients requiring follow-up (gaps in care).
- An ability for insurers to adjust aspects of the healthcare plan to reward patients who use lower-cost healthcare options. For example, the insurer might adjust the healthcare plan to cover physical therapy because 15 physical therapy visits cost the same or less than 5 visits to an orthopedist.
- An ability for doctors' group practices to raise their overall measure of quality by providing uniform standards and benchmarks in response to their KPI's.

Physician Weighting Model Using User-Defined Weights

In the preferred embodiment, the user 121 can also apply a range of numeric point values to each KPI or for a group of KPIs. The user 121 can assign the same point value across all KPIs or assign a different value for each KPI, depending on the user's preference. The weight or point value assigned by the user 121 to each KPI or group of KPIs can then determine the overall average composite score for an individual provider, a provider specialty, or an aggregation of all provider specialties.

For example, the maximum number of points for each provider is based on the point value assigned to each KPI multiplied by their average actual point score per KPI. The average actual point score per KPI per provider is either above average, average, or below average with respect to a set of comparable providers or a target minimum or maximum threshold.

The sum of the products of a provider's points by the user-defined weight per KPI across a group of individual KPIs is then divided by the sum of the weights for this group of KPIs (the sum of the maximum number of points that provider could have achieved with above average scores across the group of KPIs). This calculation determines the provider's raw composite score.

After reading this application, those skilled in the art will recognize that these additional capabilities are illustrative and in no way limiting.

ALTERNATIVE EMBODIMENTS

Although preferred embodiments are disclosed herein, many variations are possible which remain within the concept, scope, and spirit of the invention. These variations would become clear to those skilled in the art after perusal of this application:

Doctor search for patients with conditions or surgeries and/or procedure he performed on patients.

Look up doctor by quality rating measure (KPI) that are mapped to health categories or conditions.

After reading this application, those skilled in the art will recognize that these alternative embodiments are illustrative and in no way limiting.

The invention claimed is:

1. A computer implemented method, comprising:

providing a computer user interface configured to allow a user to specify a medical condition or treatment, and one or more scoring domains;

providing information about a plurality of medical providers, wherein at least some of the plurality of medical providers have bucket rankings which are statistically valid with respect to the plurality of medical providers according to a pre-selected statistically defined confidence level indicating the reliability of the bucket rankings, and wherein each bucket ranking corresponds to a scoring domain specified by the user;

selecting, using a computer apparatus, one or more providers from the plurality of providers in accordance with the condition or treatment and the one or more scoring domains specified by the user; and presenting the selected one or more medical providers, each with their respective bucket rankings, if any, to the user, wherein providing information about a plurality of medical providers further comprises determining bucket rankings for the plurality of medical providers, wherein the information about a plurality of medical providers includes a set of KPI (Key Performance Indicator) values for each of the plurality of medical providers, each KPI value indicating a measure of quality for one of the plurality of medical providers, wherein each scoring domain includes one or more KPIs, and wherein determining the bucket rankings further comprises determining, for each bucket ranking, based on a set of KPI values corresponding to KPIs included in the scoring domain to which the bucket ranking corresponds, and based on a statistically defined confidence level, a ranking of a selected one of the plurality of the medical providers, with respect to the scoring domain to which the bucket ranking corresponds, compared to the remaining medical providers of the plurality of medical providers.

2. The method of claim 1, wherein the bucket rankings relate to an overall quality of each of the plurality of medical providers.

3. The method of claim 2, wherein the bucket rankings are specific to a medical condition or treatment.

4. The method of claim 1, wherein the bucket rankings relate to an overall cost effectiveness of each of the plurality of medical providers.

5. The method of claim 4, wherein the bucket rankings are specific to a medical condition or treatment.

6. The method of claim 1, wherein the selection of the one or more medical providers is responsive to updates of records regarding the plurality of medical providers.

7. The method of claim 1, wherein the bucket rankings are represented by a graphical rating.

8. A non-transitory computer-readable medium storing software comprising instructions executable by one or more processing devices which, upon such execution, cause the one or more processing devices to perform operations comprising:

providing a computer user interface configured to allow a user to specify a medical condition or treatment, and one or more scoring domains;

providing information about a plurality of medical providers, wherein at least some of the plurality of medical providers have bucket rankings which are statistically valid with respect to the plurality of medical providers according to a pre-selected statistically defined confidence level indicating the reliability of the bucket rankings, and wherein each bucket ranking corresponds to a scoring domain specified by the user;

selecting, using a computer apparatus, one or more providers from the plurality of providers in accordance with the condition or treatment and the one or more scoring domains specified by the user; and presenting the selected one or more medical providers, each with their respective bucket rankings, if any, to the user, wherein providing information about a plurality of medical providers further comprises determining bucket rankings for the plurality of medical providers, wherein the information about a plurality of medical providers includes a set of KPI (Key Performance Indicator) values for each of the plurality of medical providers, each KPI value indicating a measure of quality for one of the plurality of medical providers, wherein each scoring domain includes one or more KPIs, and wherein determining the bucket rankings further comprises determining, for each bucket ranking, based on a set of KPI values corresponding to KPIs included in the scoring domain to which the bucket ranking corresponds, and based on a statistically defined confidence level, a ranking of a selected one of the plurality of the medical providers, with respect to the scoring domain to which the bucket ranking corresponds, compared to the remaining medical providers of the plurality of medical providers.

9. The computer-readable medium of claim 8, wherein the bucket rankings relate to an overall quality of each of the plurality of medical providers.

10. The computer-readable medium of claim 9, wherein the bucket rankings are specific to a medical condition or treatment.

11. The computer-readable medium of claim 8, wherein the bucket rankings relate to an overall cost effectiveness of each of the plurality of medical providers.

12. The computer-readable medium of claim 11, wherein the bucket rankings are specific to a medical condition or treatment.

13. The computer-readable medium of claim 8, wherein the selection of the one or more medical providers is responsive to updates of records regarding the plurality of medical providers.

14. The computer-readable medium of claim 8, wherein the bucket rankings are represented by a graphical rating.

15. A system comprising:

one or more data processors; and a non-transitory computer-readable medium coupled to the one or more data processors having instructions stored thereon which, when executed by the one or more data processors, cause the one or more data processors to perform operations comprising:

providing a computer user interface configured to allow a user to specify a medical condition or treatment, and one or more scoring domains;

providing information about a plurality of medical providers, wherein at least some of the plurality of medical providers have bucket rankings which are statistically valid with respect to the plurality of medical providers according to a pre-selected statistically defined confidence level indicating the reliability of the bucket rankings, and wherein each bucket ranking corresponds to a scoring domain specified by the user;

selecting, using a computer apparatus, one or more providers from the plurality of providers in accordance with the condition or treatment and the one or more scoring domains specified by the user; and presenting the selected one or more medical providers, each with their respective bucket rankings, if any, to the user wherein providing information about a plurality of medical providers further comprises determining bucket rankings for the plurality of medical providers, wherein the information about a plurality of medical providers includes a set of KPI (Key Performance Indicator) values for each of the plurality of medical providers, each KPI value indicating a measure of quality for one of the plurality of medical providers, wherein each scoring domain includes one or more KPIs, and wherein determining the bucket rankings further comprises determining, for each bucket ranking, based on a set of KPI values corresponding to KPIs included in the scoring domain to which the bucket ranking corresponds, and based on a statistically defined confidence level, a ranking of a selected one of the plurality of the medical providers, with respect to the scoring domain to which the bucket ranking corresponds, compared to the remaining medical providers of the plurality of medical providers.

* * * * *